(12) United States Patent
Hyoda et al.

(10) Patent No.: US 6,433,181 B1
(45) Date of Patent: Aug. 13, 2002

(54) PROCESS FOR THE PREPARATION OF HIGHLY PURE 5,5'-BI-1H-TETRAZOLEDIAMMONIUM SALTS

(75) Inventors: Shunji Hyoda; Masaharu Kita; Atsushi Sugino; Shuichi Nemugaki; Takahiro Ueta; Koki Sato, all of Sakaide (JP)

(73) Assignees: Japan Hydrazine Co. Ltd., Tokyo; Masuda Chemical Industry Co, Ltd., Kagawa-ken, both of (JP)

( * ) Notice: Subject to any disclaimer, the term of this patent is extended or adjusted under 35 U.S.C. 154(b) by 0 days.

(21) Appl. No.: 09/871,946

(22) Filed: Jun. 4, 2001

(30) Foreign Application Priority Data

Jun. 5, 2000 (JP) ........................ 2000-168213

(51) Int. Cl.$^7$ ...................... C07D 257/04; C07D 403/04
(52) U.S. Cl. ....................................... 548/250
(58) Field of Search ......................... 548/250

(56) References Cited

U.S. PATENT DOCUMENTS

| 2,710,297 A | * | 1/1955 | Friederich et al. | .......... 260/308 |
| 6,040,453 A | * | 3/2000 | Hyoda et al. | ............... 548/250 |
| 6,156,906 A | * | 12/2000 | Hyoda et al. | ............... 548/250 |

* cited by examiner

*Primary Examiner*—Robert W. Ramsuer
*Assistant Examiner*—Golam M. M. Shameem
(74) *Attorney, Agent, or Firm*—Sherman & Shalloway

(57) ABSTRACT

A process for the preparation of a highly pure 5,5'-bi-1H-tetrazolediammonium salt comprising adding a small amount of ammonia water to a reaction solution containing a 5,5'-bi-1H-tetrazolediammonium salt synthesized in the presence of a copper catalyst, removing by filtration the blue insoluble components of formed copper.ammonia.5,5'-bi-1H-tetrazole complex to obtain a filtrate of the 5,5'-bi-1H-tetrazoledisodium salt and reacting the filtrate with an aqueous solution of ammonium chloride, and recovering the formed, highly pure ammonium salt as sparingly soluble crystals.

21 Claims, No Drawings

PROCESS FOR THE PREPARATION OF HIGHLY PURE 5,5'-BI-1H-TETRAZOLEDIAMMONIUM SALTS

BACKGROUND OF THE INVENTION 1. (Field of the Invention)

The present invention relates to a process for the preparation of 5,5'-bi-1H-tetrazolediammonium salts. (BHT.2NH₃) which are lowly toxic, easy to handle, and are useful as gas-generating agents for air bags and as high-molecular foaming agents.

2. (Prior Art)

5,5'-Bi-1H-tetrazoles (BHT) or salts thereof have a chemical structure expressed by the following formula (1),

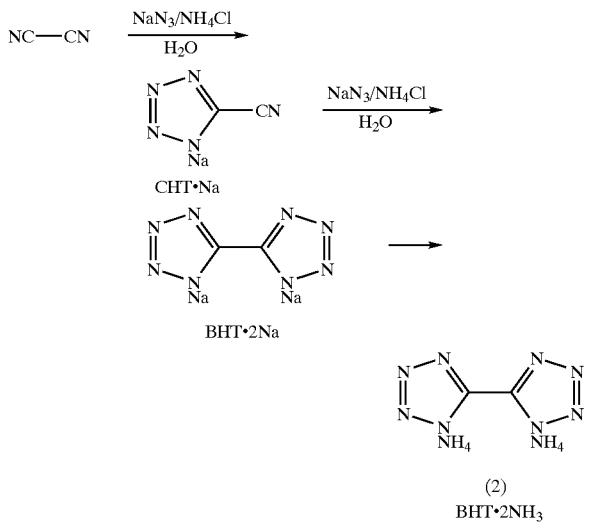

wherein X is a hydrogen atom or a cation pair.

The following prior arts 1 and 2 have been known for synthesizing these compounds.

(Prior Art 1) Japanese Laid-Open Patent Application No. 2000-256332, U.S. Pat. No. 6,040,453 (2000).

The present invention inventors have already proposed the synthesis of a 5,5'-bi-1H-tetrazolediammonium salt from a dicyan and an aqueous solution of sodium azide/ammonium chloride by a reaction expressed by the following formula (2),

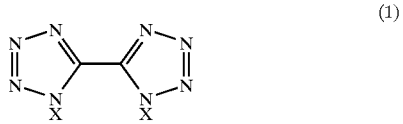

(Prior Art 2) Japanese Laid-Open Patent Application No. 2000-191649.

The present inventors have proposed the synthesis of a 5,5'-bi-1H-tetrazolediammonium salt (BHT.2NH₃) from hydrogen cyanide, sodium azide and aqueous hydrogen peroxide by a reaction expressed by the following formula (3),

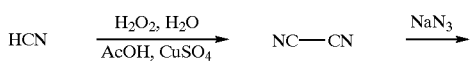

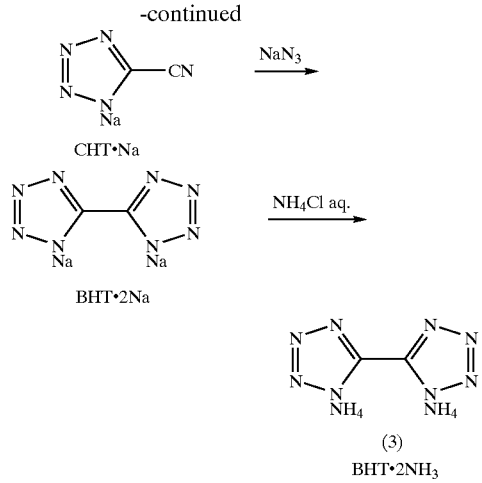

in the presence of a catalytic amount of copper sulfate while adjusting the pH of the reaction solution to be 5 to 6 by the addition of an organic acid such as acetic acid or formic acid.

According to the prior art 1, a 5,5'-bi-1H-tetrazolediammonium salt is synthesized by the heat cyclization reaction of the dicyan as a starting material with an aqueous solution of sodium azide/ammonium chloride.

This method, however, involves such defects as toxicity, use of the dicyan which is difficult to handle as a starting material, and an additional provision of a step for synthesizing the dicyan causing the reaction apparatus to become complex.

The prior art 2 is to isolate the 5,5'-bi-1H-tetrazolediammonium salt in the form of sparingly soluble crystals by the one-pot reaction by using hydrogen cyanide and sodium azide as starting materials while using copper sulfide as a catalyst and aqueous hydrogen peroxide as an oxidizing agent.

However, the obtained course crystals exhibit a blue color due to the presence of several thousands of ppm of copper that was used as the catalyst, and are never satisfactory concerning their purity and quality.

SUMMARY OF THE INVENTION

It is therefore an object of the present invention to provide a process for the preparation of a 5,5'-bi-1H-tetrazolediammonium salt (BHT.2NH₃) containing very decreased amounts of impurities such as of copper from a reaction solution containing a 5,5'-bi-1H-tetrazoledisodium salt synthesized in the presence of a copper catalyst.

Another object of the present invention is to provide a method of efficiently synthesizing a highly pure 5,5'-bi-1H-tetrazolediammonium salt (BHT.2NH₃) through a decreased number of steps, i.e., through the one-pot reaction from the starting materials that are cheaply available and are easy to handle.

According to the present invention, there is provided a process for the preparation of a highly pure 5,5'-bi-1H-tetrazolediammonium salt by adding a small amount of aqueous ammonia to a reaction solution containing a 5,5'-bi-1H-tetrazoledisodium salt synthesized in the presence of a copper catalyst, by reacting an aqueous solution of ammonium chloride with a filtrate of the 5,5'-bi-1H-tetrazoledisodium salt obtained by removing by filtration the blue insoluble components of the formed copper.ammonia.5,5'-bi-1H-tetrazole complex, and by recovering the formed highly pure ammonium salts as sparingly soluble crystals.

According to the present invention, the reaction solution containing the 5,5'-bi-1H-tetrazoledisodium salt is obtained by synthesizing a dicyan by adding, as an oxidizing agent, a aqueous hydrogen peroxide to an aqueous solution of the starting materials of which the pH has been adjusted to be 5 to 7 by the addition of a small amount of acidic substance in the presence of hydrogen cyanide or sodium cyanide, sodium azide and a catalytic amount of a copper salt, followed by the heat-cyclization reaction.

It is further allowable to form a complex by adding a small amount of aqueous hydrogen peroxide together with a small amount of aqueous ammonia to the reaction solution that contains the 5,5'-bi-1H-tetrazoledisodium salt.

It is further desired to put the filtrate obtained by removing by filtration the blue insoluble components of the formed copper.ammonia.5,5-bi-1H tetrazole complex to the treatment with a chelating resin, followed by the reaction with an aqueous solution of ammonium chloride.

It is further allowable to react the reaction solution containing the 5,5'-b-1H-tetrazoledisodium salt with the aqueous solution of ammonium chloride, separate the formed 5,5'-bi-1H-tetrazolediammonium salt as copper-containing coarse crystals, react the course diammonium salt crystals with the aqueous solution of sodium hydroxide to convert it into an aqueous solution of the 5,5'-bi-1H-tetrazoledisodium salt which is dissolved therein, and remove by filtration the blue insoluble component of the copper.ammonia.5,5'-bi-1H-tetrazole complex, followed by refining by the treatment with a chelating resin.

According to the present invention, it is desired that the molar ratio of the hydrogen peroxide water added to the aqueous solution of starting material is increased so that the catalytic amount of copper salt migrates into the coarse 5,5'-bi-1H-tetrazolediammonium salt crystals that are to be separated, that the aqueous hydrogen peroxide is added to the reaction for the synthesis of the 5,5'-bi-1H-tetrazoledisodium salt in such an amount that the molar ratio (E/A) of the aqueous hydrogen peroxide (E) to the hydrogen cyanide or the sodium cyanide (A) used for the synthesis is from 0.5 to 0.8, and that, after the reaction of synthesizing the 5,5'-bi-1H-tetrazoledisodium salt, the hydrogen peroxide water is added to the reaction in such an amount that the molar ratio (H/A) of the aqueous hydrogen peroxide (H) to the hydrogen cyanide or the sodium cyanide (A) used for the synthesis is from 0.001 to 0.20.

It is further desired that the amount of the aqueous ammonia added to the reaction solution of the 5,5'-bi-1H-tetrazoledisodium salt is such that the molar ration (G/A) of the ammonia (G) to the hydrogen cyanide or the sodium cyanide (A) used for the synthesis is from 0.01 to 0.16.

As the acidic substance, there can be used organocarboxylic acids such as actic acid and formic acid, or mineral acids such as hydrochloric acid, sulfuric acid and nitric acid.

In the present invention, it is desired that the treatment with the chelating resin is conducted at a temperature of not lower than 40° C.

DETAILED DESCRIPTION OF THE INVENTION

In the present invention, a small amount of aqueous ammonia or a smaller amount of aqueous hydrogen peroxide is added to the reaction solution containing a 5,5'-bi-1H-tetrazoledisodium salt synthesized in the presence of a copper catalyst in order to separate the copper component in the reaction solution as a blue insoluble component of the copper.ammonia.5,5'-bi-1H-tetrazole complex.

That is, copper which is the catalyst and is a chief impurity component is removed by filtration as a blue insoluble component of the copper.ammonia.5,5'-bi-1H-tetrazole complex. Thus, most of copper in the coarse or crude crystals or in the reaction solution is easily removed and, hence, the copper content is decreased to 5 to 35 ppm in the 5,5'-bi-1H-tetrazolediammonium salt (BHT.2NH$_3$) crystals obtained by the reaction with the aqueous solution of ammonium chloride.

Upon conducting the operation for refining the filtrate from which the insoluble components have been removed or for refining the solution in which coarse or crude crystals have been dissolved again with the chelating resin, further, it is allowed to prepare, at a high yield, a highly pure 5,5'-bi-1H-tetrazolediammonium salt having a copper content of 1 to 3 ppm as a result of removing copper that greatly deteriorates the stability of the 5,5'-bi-1H-tetrazolediammonium salt (BHT.2NH$_3$) used as a gas-generating agent for air bags.

The process of the invention will now be described in detail. There can be exemplified the following five representative examples A to E for preparing the highly pure 5,5'-bi-1H-tetrazolediammonium salt (BHT.2NH$_3$) according to the invention.

(A)

(1) The 5,5'-bi-1H-tetrazoledisodium salt (BHT.2Na) is obtained by synthesizing a dicyan by adding a aqueous hydrogen perioxide to an aqueous solution of the starting materials to which a small amount of acidic substance has been added in the presence of hydrogen cyanide, sodium azide and a catalytic amount of a copper salt such as copper sulfate or copper acetate, followed by the heat-cyclization reaction;

(2) a small amount of ammonia water is added to the reaction solution that contains the 5,5'-bi-1H-tetrazoledisodium salt (BHT.2Na) to remove by filtration the blue insoluble component of the formed copper.ammonia.5,5'-bi-1H-tetrazole complex; and (3) the obtained filtrate of the 5,5-bi-1H-tetrazoledisodium salt (BHT.2Na) is reacted with an aqueous solution of ammonium chloride.

(B)

The filtrate of the 5,5'-bi-1H-tetrazoledisodium salt (BHT.2Na) obtained through the operation (A) above is refined with a chelating resin, and the treated solution is reacted with the aqueous solution of ammonium chloride, (C)

(1) Small amounts of the aqueous hydrogen peroxide and the aqueous ammonia are added to the reaction solution containing the 5,5'-bi-1H-tetrazoledisodium salt (BHT.2Na) obtained through the operation (A) (1) above in order to remove by filtration the blue insoluble component of the formed copper.ammonia.5,5'-bi-1-H-tetrazole complex; and (2) the obtained filtrate of 5,5'-bi-1H-tetrazoledisodium salt (BHT.2Na) is reacted with the aqueous solution of ammonium chloride.

(D)

(1) The reaction solution containing the 5,5'-bi-1H-tetrazoledisodium salt (BHT.2Na) obtained through the operation (A) (1) above is reacted with the aqueous solution of ammonium chloride to separate coarse crystals of 5,5'-bi-1H-tetrazolediammonium salt (BHT.2NH$_3$), and the coarse diammonium crystals are dissolved again in the aqueous solution of sodium hydroxide to remove by filtration the blue insoluble component of the formed copper.ammonia.5,5'-bi-1H-tetrazole complex; and (2) the obtained filtrate of 5,5'-bi-1H-tetrazoledisodium salt (BHT.2Na) is reacted with the aqueous solution of the ammonium chloride, or the solution of 5,5'-bi-1H-tetrazoledisodium salt (BHT.2Na) obtained by refining the filtrate with the chelating resin is reacted with the aqueous solution of ammonium chloride.

(E)
(1) A small amount of aqueous ammonia is added or small amounts of aqueous hydrogen peroxide and aqueous ammonia are added to the reaction solution containing 5,5'-bi-1H-tetrazoledisodium salt (BH[].2Na) obtained through the above operation (A) (1) in order to remove by filtration the blue insoluble component of the formed copper.ammonia.5,5'-bi-1H-tetrazole complex;

(2) the obtained filtrate of 5,5'-bi-1H-tetrazoledisodium salt (BHT.2Na) is reacted with the aqueous solution of ammonium chloride to separate the crystals of 5,5-bi-1H-tetrazolediammonium salt (BHT.2NH$_3$);

(3) the diammonium salt (BHT.2NH$_3$) crystals are dissolved again in the aqueous solution of sodium hydroxide and are refined with the chelating resin; and (4) the obtained treated solution of 5,5'-bi-1H-tetrazoledisodium salt (BHT.2Na) is reacted with the aqueous solution of ammonium chloride.

Through the combination of the above methods, the highly pure 5,5'-bi-1H-tetrazolediammonium salt (BHT.2NH$_3$) is synthesized.

The 5,5'-bi-1H-tetrazolediammonium salt (BHT.2NH$_3$) prepared according to the present invention is obtained in the form of highly pure white crystals having a purity of not lower than 99% and a copper content of 1 to 5 ppm or smaller, maintaining an yield of as high as about 80%.

The invention provides a process for the preparation of 5,5'-bi-1H-tetrazolediammonium salts of a high purity maintaining a high yield using cheaply and easily available starting materials through very simple reactions and refining operation.

Though not necessarily limited thereto only it is considered that the reaction mechanism according to the present invention proceeds as expressed by the following formula (4). Further, the refining operation can be conducted by any one of the following five methods A to E in the formula (4).

Reaction steps

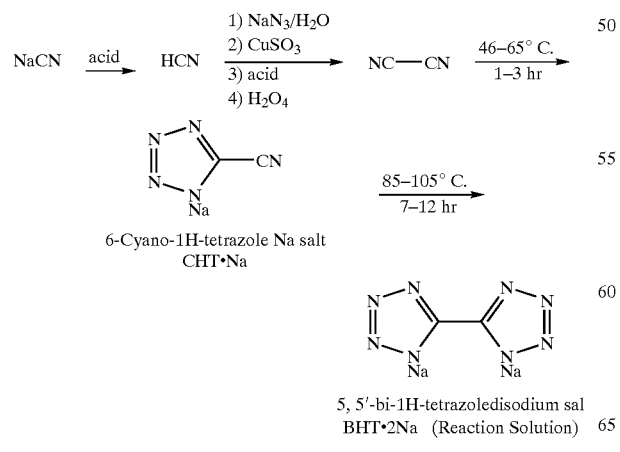

6-Cyano-1H-tetrazole Na salt
CHT·Na 5, 5'-bi-1H-tetrazoledisodium sal
BHT·2Na (Reaction Solution)

Formula (4)

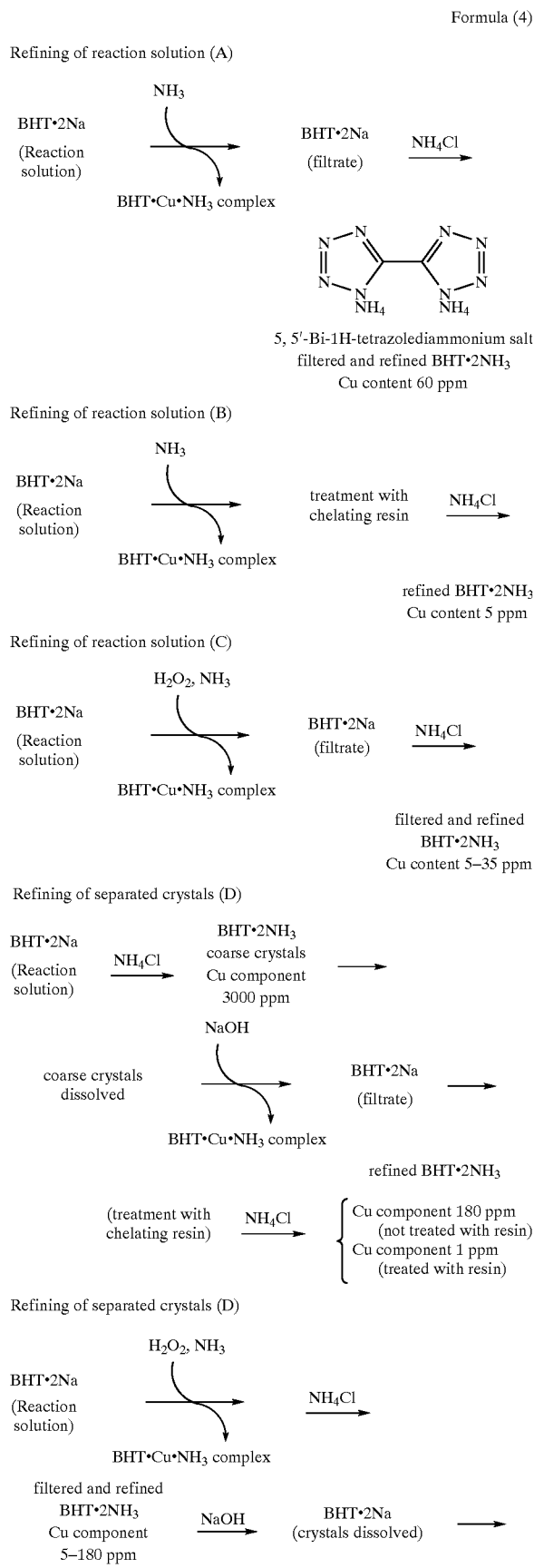

(treatment with chelating resin) 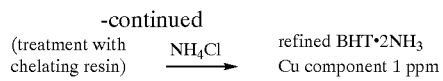 NH₄Cl → refined BHT·2NH₃ Cu component 1 ppm In the reaction for synthesizing the 5,5'-bi-1H-tetrazolediammonium salt (BHT.2NH₃) according to the invention, a reaction solution containing a 5,5'-bi-1H-tetrazoledisodium salt (BHT.2Na) is obtained by a simple one-pot synthesizing route by adding a small amount of hydrochloric acid or the like acid, as an acidic substance, to an aqueous solution of starting materials containing hydrogen cyanide, sodium azide and a catalytic amount of copper salt to adjust the pH to be 5 to 7 and, then, adding the aqueous hydrogen peroxide and heating the reaction solution to synthesize the dicyan and to effect the ring-closing reaction.

According to the present invention, it is desired that the aqueous solution containing the starting materials is prepared at a temperature as slow as possible and, generally, at a temperature of not higher than 20° C. This effectively prevents the side reaction and, further, prevents the leakage of hydrogen cyanide.

There is no particular limitation on the method of preparing the aqueous solution of the starting materials used in the invention so far it has the composition as described above. Preferred preparation methods are as described below to which only, however, the invention is in no way limited.

(1) A catalytic amount of copper salt is added to the aqueous solution of sodium azide in a cooled state and, then, the hydrogen cyanide is added thereto to prepare an aqueous solution of the starting materials (see Example 15).

(2) An acid equivalent to the alkali cyanide is added to a system containing sodium cyanide, sodium azide and water in a cooled state, and a catalytic amount of copper salt is added to the obtained aqueous solution to prepare an aqueous solution of the starting materials. As the acid, there can be used mineral acids such as hydrochloric acid and the like acid.

Next, the acidic substance must be added for adjusting the pH value. Here, however, the acidic substance may be added together with an acid that is added for neutralizing the sodium cyanide. As the alkali cyanide, there can be used sodium cyanide or potassium cyanide. This gives such an advantage that the starting cyan is easily available and is easy to handle.

As the source of hydrogen cyanide, there can be used hydrogen cyanide, sodium cyanide, potassium cyanide and acetone cyanhydrin. In any one of the above methods, the aqueous solution of sodium cyanide must have been neutralized with an acid in advance when the sodium cyanide and the copper salt are to be mixed together in the aqueous solution.

When the neutralization is not conducted to a sufficient degree, the polymerization reaction of cyan, which is a side reaction, takes place at the time of preparing the aqueous solution of the starting materials, and the yield decreases. It is desired to maintain the temperature of the reaction system in a range of from 0 to 20° C. even from the standpoint of preventing the side reaction.

In the present invention, it is desired that the aqueous solution of the starting materials is so prepared that the molar ratio (B/A) of the sodium azide (B) to the hydrogen cyanide or the sodium cyanide (A) is from 0.1 to 1.5 from the standpoint of yield and purity.

In the present invention, it is important to maintain the pH of the reaction solution in a range of 5 to 7 by adding a small amount of acidic substance to the above water solution of the starting materials. When pH <5, the 5,5'-bi-1H-tetrazole (BHT) which is sparingly soluble in water precipitates during the reaction. When pH>7, the polymerization reaction of the hydrogen cyanide takes place predominantly, and the 5,5'-bi-1H-tetrazoledisodium salt (BHT.2Na) is formed in only a very small amount. In the present invention, therefore, the pH is maintained in the above-mentioned range to prevent the side reaction and to improve the yield and purity.

As the acidic substance, there can be used an organocarboxylic acids as acetic acid and formic acid, as well as mineral acids such as hydrochloric acid, sulfuric acid and nitric acid. Among them, hydrochloric acid is particularly preferred. There occurs no problem in the reaction when an organocarboxylic acid such as acetic acid is used. When the treatment with a chelating resin is effected in a subsequent step for refining in a reaction solution containing the carboxylic acid, however, the ability of the chelating resin for removing copper decreases, which is not desirable.

The molar ratio of the acidic substance that is added is to adjust the pH as described above. Here, it is desired to so add the acidic substance that the molar ratio (C/A) of the acidic substance (C) to the hydrogen cyanide or the sodium cyanide (A) is from 0.05 to 0.3.

In the present invention, a divalent copper salt such as copper sulfate or copper acetate can be used as a copper salt catalyst for the reaction. As for the molar ratio of addition, it is desired that the copper salt (D) is made present at a molar ratio (D/A) of 0.001 to 0.1 relative to the hydrogen cyanide or the sodium cyanide (A) from the standpoint of yield and purity.

In the present invention, the aqueous hydrogen peroxide is added at a temperature of 0 to 90° C. and, preferably, at 30 to 50° C. When the aqueous hydrogen peroxide is added at a low temperature which is not higher than 10° C., the reaction by hydrogen peroxide does not proceed smoothly. Therefore, the unreacted hydrogen peroxide builds up in the reaction solution despite it is dropwisely added at a small rate, often resulting in the occurrence of a sudden explosive reaction to generate heat. When the reaction temperature exceeds 90° C., the yield drops greatly. It is therefore desired that hydrogen peroxide is gradually added at nearly 40° C.

The molar ratio (E/A) of the hydrogen peroxide (E) that is added is 0.5 to 0.8 and, preferably, 0.55 to 0.6 relative to the hydrogen cyanide or the sodium cyanide (A). When this molar ratio increases, copper used as the catalyst mostly remains in the coarse 5,5'-bi-1H-tetrazolediammonium salt crystals. When this molar ratio decreases, on the other hand, copper remains in an increased amount in the separated mother liquor.

In the present invention, after the aqueous hydrogen peroxide has been added, the reaction solution is heated to execute the dimerization and the ring-closing reaction by oxidation. It is desired that the heating is conducted in two stages at 40 to 60° for 1 to 3 hours and at 85 to 105° C for 4 to 12 hours.

Tracing using the liquid chromatography indicates that the reaction in the preceding stage forms a 5-cyano-1H-tetrazolesodium salt (CHT.Na) intermediate product and the reaction in the succeeding stage converts the above intermediate product into a 5,5'-bi-1H-tetrazoledisodium salt (BHT.2Na). It is desired that the reaction is conducted until the amount of the intermediate product becomes smaller than 1% (area percentage by the liquid chromatography).

In the present invention, the 5,5'-bi-1H-tetrazolediammonium salt (BHT.2NH₃) is isolated by reacting the aqueous solution of ammonium chloride with a reaction solution containing the 5,5'-bi-1H-tetrazoledisodium salt (BHT.2Na), with the filtrate from which the insoluble component has been removed or with the solution after filtered and refined with the chelating resin, and recovering the formed sparingly soluble salt in the form of white crystals.

It is desired to add the ammonium chloride such that the molar ratio (F/A) of the ammonium chloride (F) to the hydrogen cyanide or the sodium cyanide (A) is 1.0 to 1.5.

In the present invention, it is desired to add the aqueous solution of ammonium chloride to the reaction solution containing the 5,5'-bi-1H-tetrazoledisodium salt (BHT.1Na), to the filtrate thereof or to the solution thereof refined with the chelating resin to conduct the reaction at room temperature to 100° C. for 1 to 3 hours from the standpoint of forming the 5,5'-bi-1H-tetrazolediammonium salt (BHT.2NH$_3$) maintaining a good yield.

By adding the aqueous solution of ammonium chloride to the reaction solution of the 5,5'-bi-1H-tetrazoledisodium salt (BHT.2Na) to react them together, the recovered coarse 5,5'-bi-1H-tetrazolediammonium salt crystals contain copper, sodium and chlorine which are impurities.

In particular, much of copper used as the catalyst remains in the coarse crystals, and the 5,5'-bi-1H-tetrazolediammonium salt, which by itself is a white compound, is recovered as blue crystals. Therefore, removal of the copper component is important for using the 5,5'-bi-1H-tetrazolediammonium salt as a gas-generating agent for air bags.

The present inventors have already proposed a process for the preparation of the 5,5'-bi-1H-tetrazolediammonium salt (BHT.2NH$_3$) (Japanese Laid-Open Patent Application No. 2000-191649). However, the coarse 5,5'-bi-1H-tetrazolediammonium salt crystals contained several hundreds to several thousands ppm of copper component, and were not satisfactory from the standpoint of either purity or quality.

It is an object of the present invention to provide a process for the preparation of highly pure 5,5'-bi-1H-tetrazolediammonium salt (BHT.2NH$_3$) by decreasing the copper content in the refined crystals down to 1 to 5 ppm by removing the blue insoluble component of copper.ammonia.5,5'-bi-1H-tetrazole complex and by effecting the refining with a chelating resin.

According to the present invention, the copper content in the refined crystals can be decreased down to 60 to 150 ppm (about 1/20 that of the coarse crystals) by simply removing by filtration the insoluble component of copper.ammonium.5, 5'-bi-1H-tetrazole complex by adding a small amount of aqueous ammonia to the reaction solution containing 5,5'-bi-1H-tetrazoledisodium salt (BHT.2Na).

Upon adding the aqueous ammonia to the reaction solution, the copper component dissolved therein is precipitated as a blue insoluble component of the copper.ammonia.5,5'-bi-1H-tetrazole complex. By removing by filtration the complex, about 90% of the copper component fed as the catalyst is removed.

The aqueous ammonia is added in such an amount that the molar ratio (G/A) of the ammonia (G) to the hydrogen cyanide or the sodium cyanide(A) is from 0.01 to 0.16 and, preferably, from 0.02 to 0.08. When the amount of addition of ammonia is small, the insoluble component of the copper.ammonia.5,5'-bi-1H-tetrazole complex precipitates in decreased amounts. When its amount is large, fine insoluble components precipitate to deteriorate the filtering performance.

After the addition, the reaction is desirably conducted at room temperature to 60° C. for 1 to 3 hours. The filtering can be effected by using a filter or by centrifugation. When the reaction solution to which the aqueous ammonia has been added is filtered, the sodium salt crystals precipitate as the temperature of the solution becomes lower than about 50° C. It is therefore desired to add a suitable amount of diluting water to maintain the concentration of the 5,5'-bi-1H-tetrazoledisodium salt to be not larger than 10% and to maintain the temperature to be about 50° C. during the treatment.

The amount of the hydrogen peroxide water added for the reaction for the synthesis of the 5,5'-bi-1H-tetrazoledisodium salt (BHT.1Na) affects the amount of precipitation of the insoluble component of the copper.ammonia.5,5'-bi-1H-tetrazole complex of when the aqueous ammonia is added after the reaction. The larger the amount of addition of the aqueous hydrogen peroxide during the reaction, the smaller the amount of copper component remaining in the filtrate.

In particulate, when the amount of addition of the aqueous hydrogen peroxide is not smaller than 0.6 in terms of a molar ratio to the sodium cyanide, the insoluble component of the copper.ammonia.5,5'-bi-1H-tetrazole complex precipitates in increased amounts. Therefore, the copper component in the filtrate can be decreased to be smaller than about 10 ppm, and the 5,5'-1H-tetrazolediammonium salt (BHT.2NH$_3$) that is obtained contains copper component in an amount of not larger than 60 ppm (see Example 1, copper component in the crystals is 59.1 ppm).

Copper of the copper.ammonia.5,5'-bi-1H-tetrazole complex that is precipitated as the insoluble component is in a state of being divalently oxidized. When copper is oxidized from a monovalent state into a divalent state with the hydrogen peroxide water, therefore, the solubility of the complex decreases and the complex is precipitated as the insoluble component.

Copper ions remaining in a monovalent form after the reaction do not form the insoluble component of the copper.ammonia.5,5-bi-1H-tetrazole complex and, hence, remain in the filtrate creating a chief cause of copper infiltration into the 5,5'-bi-1H-tetrazolediammonium salt (BHT.2NH$_3$) crystals that are obtained by the reaction with the aqueous solution of ammonium chloride.

In the present invention, the copper compound often remains in an amount of about 60 ppm in the 5,5'-bi-1H-tetrazolediammonium salt (BHT.2NH$_3$) crystals obtained by the reaction with the aqueous solution of ammonium chloride after the insoluble component of the copper.ammonia.5, 5'-bi-1H-tetrazole complex has been removed by filtration from the reaction solution containing the 5,5'-bi-1H-tetrazoledisodium salt (BHT.2Na) by the addition of a small amount of the aqueous ammonia. Upon further treating the filtrate containing the insoluble component with the chelating resin, however, trace amounts of copper component remaining in the filtrate can be removed by adsorption.

Upon the treatment with the chelating resin, the content of copper component in the 5,5'-bi-1H-tetrazolediammonium salt (BHT.2NH$_3$) crystals is decreased down to not larger than 5 ppm. According to this method, the reaction solution containing the 5,5'-bi-1H-tetrazoledisodium salt (BHT.2Na) of after the insoluble component is removed by filtration is treated with the chelating resin without separating the crystals, contributing to simplifying the steps of refining.

However, when the reaction solution containing the acetic acid that is added as the acidic substance during the reaction, is treated with the chelating resin, the resin exhibits decreased ability for adsorbing copper (see Example 7, acetic acid is used, copper content in the crystals is 76.7 ppm). This is because the acetic acid component present in the reaction solution is adsorbed by the resin which, then, loses the ability for removing the copper component. In the reaction of synthesizing the 5,5'-bi-1H-tetrazoledisodium salt (BHT.2Na), therefore, it is desired to use mineral acids such as hydrochloric acid instead of organocarboxylic acids such as acetic acid. That is, by using mineral acids as acidic substance (see Example 6, hydrochloric acid is used, copper content in the crystals is 4.9 ppm), the resin exhibits the adsorbing ability to a sufficient degree. This method does not require the step of separating coarse crystals and dissolving them again, and enables the reaction solution to be refined. However, the resin exhibits a low ability for adsorbing copper if compared with the case when the reaction solution is treated with the chelating resin after the coarse crystals are separated and are dissolved again (see Example 12, copper content in the crystals is 1.3 ppm).

According to the present invention, the copper content in the refined crystals can be decreased down to 5 to 35 ppm or less (60 to 150 ppm when the ammonia water only is added) through the simple refining processing of removing by filtration the insoluble component of the copper.ammonia.5,5'-bi-1H tetrazole complex from the reaction solution containing the 5,5'-bi-1H-tetrazoledisodium salt (BHT.2Na) by adding small amounts of the aqueous hydrogen peroxide and aqueous ammonia.

By adding the aqueous hydrogen peroxide and aqueous ammonia to the reaction solution, the copper component dissolved therein is completely oxidized into a divalent form and is precipitated as a blue insoluble component of the copper.ammonia.5,5'-bi-1H-tetrazole complex which is, then, removed by filtration. Thus, not less than 99% of the copper component fed as the catalyst is removed.

After the reaction but prior to adding the aqueous ammonia, the hydrogen peroxide water is added to such a small amount that the molar ratio (H/A) of the aqueous hydrogen peroxide (H) to the hydrogen cyanide or the sodium cyanide (A) is from 0.001 to 0.20 and, preferably, from 0.01 to 0.05. The amount of addition of the aqueous hydrogen peroxide must be large enough for oxidizing all copper which is the catalyst in the reaction solution into divalent copper ions. The amount of addition of the aqueous ammonia is the same as that of when no aqueous hydrogen peroxide is added. After the reaction but prior to adding the aqueous ammonia, a small amount of the aqueous hydrogen peroxide is added against to effect the filtering. This method is more desirable than when the aqueous ammonia only is added, and the copper component is more effectively removed (see Examples 8 and 8, copper content in the filtrate <4 ppm, copper content in the crystals is 5 to 35 ppm).

The aqueous hydrogen peroxide used for the reaction must be added in an amount in excess of the stoichiometric amount. If added at one time at the start of the reaction, the excess of aqueous hydrogen peroxide is decomposed during the reaction. It is therefore desired to add again part of the excess amount of the hydrogen peroxide after the reaction. Then, monovalent copper ions after the reaction are oxidized into divalent copper ions, and the insoluble component of the copper.ammonia.5,5'-bi-1H tetrazole complex is more easily precipitated, and the copper component is highly efficiently removed. Even when added in an excess amount for the treatment of the waste liquor, the insoluble component of the copper.ammonia.5,5'-bi-1H tetrazole complex can be removed out of the reaction system. Therefore, no operation is required for removing the copper component in the treatment of the waste liquor of the separated mother liquor.

According to the present invention, the copper component in the filtrate is greatly decreased through the simple operation of removing by filtration the blue insoluble component of the copper.ammonia.5,5'-bi-1H-tetrazole complex by adding the aqueous hydrogen peroxide and ammonia water to the reaction solution containing the 5,5'-bi-1H-tetrazoledisodium slat (BHT.2Na). The effect for removing the copper component is exhibited even by adding the ammonia water only, and the copper component is decreased down to about 60 ppm in the 5,5'-bi-1H-tetrazolediammonium salt (BHT.2NH$_3$) that is recovered by reacting the filtrate with the aqueous solution of ammonium chloride (see Example 1, copper content in the crystals is 59.1 ppm).

A higher copper-removing effect is exhibited when a small amount of the hydrogen peroxide water is added prior to adding the ammonia water. In this case, the copper content in the filtrate can be decreased down to not larger than 4 ppm, and the copper content in the crystals can be decreased down to about 5 to 35 ppm in the crystals recovered by the reaction with the aqueous solution of ammonium chloride (see Example 8, copper content in the crystals is 33.4 ppm; Example 9, copper content in the crystals is 5.0 ppm).

This method yields highly pure 5,5'-bi-1H-tetrazolediammonium salt (BHT.2NH$_3$) crystals. When it is desired to obtain crystals containing the copper component in more decreased amounts, the crystals refined by filtration are dissolved again in an aqueous solution of sodium hydroxide followed by the treatment with the chelating resin. Then, the copper content in the refined crystals is decreased down to 1 ppm or smaller (see Example 10, copper component in the crystals <1 ppm), and the 5,5'-bi-1H-tetrazolediammonium salt (BHT.2NH$_3$) can be separated in a highly pure crystalline form.

In the present invention, the reaction solution of the 5,5'-bi-1H-tetrazoledisodium salt (BHT.2Na) is reacted with the ammonium chloride or an aqueous solution thereof, the formed crystals are separated as coarse crystals of the 5,5'-bi-1H-tetrazolediammonium salt (BHT.2NH$_3$) containing impurities such as copper, sodium and chlorine, the coarse crystals are dissolved again the the aqueous solution of sodium hydroxide and, at the same time, the blue insoluble component of the copper.ammonia.5,5'-bi-1H-tetrazole complex is removed by filtration. Thus, not smaller than 90% of the copper component can be removed from the coarse crystals.

In the reaction for synthesizing the 5,5'-bi-1H-tetrazoledisodium salt (BHT.2Na), if the molar ratio of the aqueous hydrogen peroxide is increased, most of the copper component used as the catalyst remains in the coarse crystals of the 5,5'-bi-1H-tetrazolediammonium salt. If the molar ratio thereof is decreased, the copper component tends to remain in an increased amount in the separated mother liquor. By increasing the amount of addition of the aqueous hydrogen peroxide (molar ratio (E/A) of the aqueous hydrogen peroxide (E) to the hydrogen cyanide or the sodium cyanide (A) of not smaller than 0.6), therefore, the catalytic amount of copper component can be migrated into the coarse crystals of the 5,5'-bi-1H-tetrazolediammonium salt (BHT.2NH$_3$) to thereby decrease the copper component in the separated mother liquor down to several ppm (copper component in the mother liquor from which the coarse crystals are separated is 1.3 ppm when the molar ratio of the aqueous hydrogen peroxide is 0.6 (see Example 13), and the copper component in the mother liquor from which the coarse crystals are separated is 123.9 ppm when the molar ratio of the aqueous hydrogen peroxide is 0.54 (see Example 11)). Upon adding the aqueous hydrogen peroxide in an amount larger than the stoichiometric amount, no operation is required for removing the copper component in treating the waste liquor of the separated mother liquor, offering a preparation process which is industrially convenient and advantageous. From the standpoint of the yield, it is desired that the hydrogen peroxide water is added in an increased amount. By adding the aqueous hydrogen peroxide, in an amount in excess of the stoichiometric amount, it is allowed to obtain the 5,5'-1H-tetrazolediammonium salt (BHT.2NH$_3$) in a high yield. Even if the amount of addition is greatly increased (molar ratio (E/A)>0.8), however, most of the excess of hydrogen peroxide is decomposed as it is added, and no great effect is recognized in the yield.

The crystals of the 5,5'-bi-1H-tetrazolediammonium salt (BHT.2NH$_3$) are transformed into the disodium salt, the sodium hydroxide (I) to be dissolved again is added in such an amount that its molar ratio (I/BHT.2NH$_3$) to the 5,5'-bi-1H-tetrazolediammonium salt that is fed is from 2.0 to 2.6 and, preferably, from 2.0 to 2.2, thereby to transform the sparingly soluble 5,5'-bi-1H-tetrazolediammonium salt into the disodium salt that dissolves. Upon removing by filtration the copper.ammonia.5,5'-bi-1H-tetrazole complex that is precipitated as a result of dissolving the coarse crystals, the copper component in the filtrate is decreased down to about 10 ppm. By reacting the filtrate with the aqueous solution of ammonium chloride, the 5,5'-bi-1H-tetrazolediammonium salt is recovered as a sparingly soluble salt. Therefore, the 5,5'-1H-tetrazolediammonium salt crystals are obtained as pale bluish white crystals containing the copper component in an amount of about 200 ppm (see Example 2, copper content in the crystals is 180 ppm). The copper content has decreased down to 1/10 as compared to that of the course crystals. It is further possible to treat the filtrate of the complex with the chelating resin followed by the reaction with an aqueous solution of ammonium chloride to separate the 5,5'-bi-1H-tetrazolediammonium salt crystals as white crystals in which the copper content has been decreased down to about 1 to about 3 ppm.

It is desired that the coarse crystals of the 5,5'-bi-1H-tetrazolediammonium salt (BHT.2NH$_3$) are dissolved by the reaction with the sodium hydroxide at room temperature to 60° C. for 0.5 to 2 hours, that the diammonium salt is transformed into the disodium salt (BHT.2Na), and the blue insoluble component of the copper•ammonium•5,5'-bi-1H-tetrazole complex is precipitated by the reaction with the ammonia that was not consumed by the 5,5'-bi-1H-tetrazolediammonium salt. The filtering is effected by either using a filter or by a centrifuge. When the liquid temperature becomes lower than about 50° C. during the filtering, the 5,5'-bi-1H-tetrazoledisodium salt crystals precipitate. It is therefore desired to maintain the concentration of the 5,5'-bi-1H-tetrazoledisodium salt to be not larger than 10% and to maintain the temperature during the processing to be about 50° C.

According to the present invention, coarse crystals of the 5,5'-bi-1H-tetrazolediammonium salt (BHT.2NH$_3$) are dissolved by the reaction with the sodium hydroxide, the blue insoluble component of the copper•ammonia•5,5'-bi-1H-tetrazole complex is removed by filtration and, then, the reaction solution is reacted with the aqueous solution of ammonium chloride to obtain the 5,5'-bi-1H-tetrazolediammonium salt (BHT.2NH$_3$) crystals containing about 200 ppm of the copper component. The filtrate from which the insoluble component is removed is then treated with the chelating resin in order to remove by adsorption trace amounts of the copper component remaining in the filtrate (see Example 12, copper content in the crystals is 1.3 ppm).

According to the present invention, the filtrate obtained by removing by filtration the blue insoluble component of the copper•ammonia•5,5'-bi-1H-tetrazole complex from the reaction solution of the 5,5'-bi-1H-tetrazoledisodium salt (BHT.2Na), is reacted with the aqueous solution of ammonium chloride, and the crystals recovered by filtration are dissolved again in the aqueous solution of sodium hydroxide. This solution, too, is treated with the chelating resin so that the copper content in the 5,5'-bi-1H-tetrazolediammonium salt crystals decreases down to abut 1 to about 3 ppm (Example 10, crystals refined by filtration are dissolved again and are treated with the resin, copper content in the crystals<1 ppm).

As the resin, there can be used a chelate resin of the polyamine type or the iminodiacetic acid type. The polyamine type chelating resin (Diaion) CR-20 (produced by Mitsubishi Chemical Co.) was compared with the iminodiacetic acid type chelating resin (Diaion) CR-11 (produced by Mitsubishi Chemical Co.). After the reaction, the insoluble component was removed by filtration, the filtrate was treated with the chelating resin and was, then, reacted with the aqueous solution of ammonium chloride to compare the contents of copper in the 5,5'-bi-1H-tetrazolediammonium salt (BHT.2NH$_3$) crystals. The content of copper decreased in order of several thousand ppm in the case of coarse crystals, 180 ppm in the case when the coarse crystals were dissolved again and the insoluble component was separated (see Example 3), 9.5 ppm in the case when the filtrate was treated with the iminodiacetic acid type chelating resin (CR-11, see Example 5) and 1.1 ppm in the case when the filtrate was treated with the polyamine type chelating resin (CR-20, see Example 4). The polyamine type chelating resin exhibited particularly excellent properties.

As for the method of treating the resin, the pretreatment was conducted in a customary manner, the chelating resin was filled in a column, and the filtrate from which the insoluble component of the copper•ammonia•5,5'-bi-1H-tetrazole complex has been removed was passed through the column. It is desired that the flow velocity (SV) is maintained at 1 to 10 and the temperature at 40 to 60° C.

In conducting the treatment with the chelate resin, and in passing the solution to be treated through the column like passing the filtrate from which the blue insoluble component of the copper•ammonia•5,5'-bi-1H-tetrazole complex has been removed, the 5,5'-bi-1H-tetrazoledisodium salt (BHT.2Na) crystals precipitate when the liquid temperature becomes lower than about 50° C. It is therefore desired to maintain the concentration of the disodium salt to be not larger than 10% and the temperature during the treatment to be near 50° C.

It is desired that the column is filled with the chelating resin in an amount to exhibit the adsorbing ability 1 to 10 times as much and, preferably, 3 to 5 times as much as the amount of the copper component. The ability for removing the copper component increases with an increase in the amount of the resin, as a matter of course. The used chelating resin can be put to an ordinary regeneration treatment to use it again (see Example 18, copper content in the crystals is 1.8 ppm).

According to the present invention, the copper content in the filtrate can be decreased down to about 5 to about 35 ppm by the simple operation of removing by filtration the blue insoluble component of the copper•ammonia•5,5'-bi-1H-tetrazole complex by adding the aqueous hydrogen peroxide and the aqueous ammonia to the reaction solution that contains the 5,5'-bi-1H-tetrazoledisodium salt (BHT.2Na). The copper content is decreased down to not larger than 1 ppm in the filtrate obtained by removing the insoluble component from the reaction solution or in the solution obtained by treating the solution in which the 5,5'-bi-1H-tetrazolediammonium salt (BHT.2NH$_3$) crystals are dissolved with the chelating resin. By reacting the treated solution with the ammonium chloride crystals or with the aqueous solution thereof, the recovered 5,5'-bi-1H-tetrazolediammonium salt contains copper in an amount of 1 to 5 ppm or less (see Example 8, copper content in the crystals<1 ppm) and are obtained in the form of white and highly pure ammonium salt crystals.

The process for preparing the 5,5'-bi-1H-tetrazolediammonium salt (BHT.2NH$_3$) according to the present invention is schematically illustrated below.

lyzed by the liquid chromatography, and the hydrogen cyanide was analyzed by the gas chromatography. The content of the 5,5'-bi-1H-tetrazolediammonium salt (BHT.2NH$_3$) was found by the non-aqueous titration with HClO$_4$ and by the liquid chromatography, and metal impurities such as of copper were found by the atomic absorption analysis.

Example 1

Refining the 5,5'-bi-1H-tetrazolediammonium salt (BHT.2NH$_3$) by Filtration 195.69 Grams (3.001 mols) of 99.7% NaN$_3$, 152.57 g (3.001 mols) of 96.4% NaCN, and 876.83 g of water were fed into a 3-liter flask and were cooled down to a temperature of not higher than 10° C. to form a homogeneous aqueous solution thereof to which was then added dropwise 339.9 g (3.30 mols) of 35.4% HCl at a dropping temperature of 0.1 to 8.3° C. over a dropping time of 30 minutes to neutralize the NaCN solution. An aqueous solution contain-

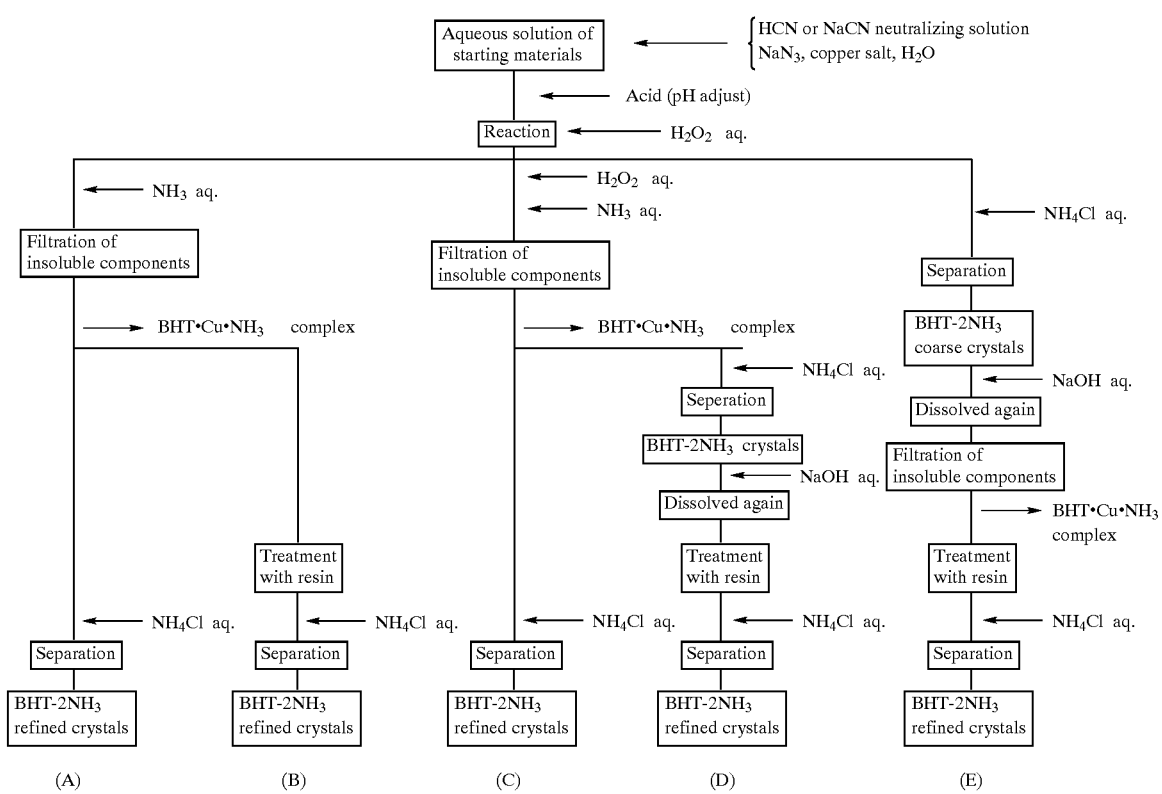

As the source of hydrogen cyanide used for the reaction of the present invention, there can be used any one of hydrogen cyanide, sodium cyanide, potassium cyanide, sodium azide, hydrogen peroxide, copper sulfate, copper acetate, hydrochloric acid, acetic acid, ammonia or sodium hydroxide, which are industrially produced products.

EXAMPLES

The invention will now be concretely described by way of Examples to which only, however, the invention is no way limited.

The 5,5'-bi-1H-tetrazole (BHT), 5-cyano-1H-tetrazole (CHT) intermediate product and hydrogen azide were anaing 3.76 g (0.015 mols) of 99.5% CuSO$_4$.5H$_2$O/17.53 g of H$_2$O was added thereto. Next, 176.90 g (1.80 mols) a 34.6% H$_2$O$_2$ aqueous solution was added thereto dropwise at a dropping temperature of 2.8 to 32.5° C. over a dropping time of one hour and 30 minutes. A green reaction solution after the starting materials have been added thereto dropwise was heated up to 40° C. over 40 minutes. The reaction was conducted at a temperature of 40.9 to 42.0° C. for 2 hours with stirring while being heated to synthesize chiefly a 5-cyano-1H-tetrazolesodium salt [CHT.Na] intermediate product. Thereafter, the temperature was raised to 90° C. over 45 minutes, and the reaction was conducted at a temperature of 87.2 to 90.6° C. for 2 hours, and was further conducted in a heated and refluxing manner (100.0 to 103.7°

C.) for 5 hours. The HPLC analysis of the reaction solution showed 97.45% of the 5,5'-bi-1H-tetrazole [BHT] and 0.88% of the 5-cyano-1H-tetrazole [CHT]. The reaction solution was cooled down to room temperature to obtain 1749.24 g of the reaction solution containing a 5,5'-bi-1H-tetrazoledisodium salt. 574.2 Grams of the reaction solution divided into one-third was heated at 50° C., 2.57 g (0.039 mols) of 26.1% aqueous $NH_3$ [8 equivalent of $CuSO_4$ that was fed]/111.1 g of water were added thereto, and the solution was stirred at a temperature of 50° C. for one hour to precipitate a blue insoluble component of the BHT.$Cu.NH_3$. The reaction solution was hot-filtered and was washed with 36.6 g of $H_2O$ to separate the insoluble component and to obtain 712.64 g of the filtrate. The filtrate was heated at 80° C., and an aqueous solution of 58.48 g (1.082 mols) of 99.0% $NH_4Cl$/166.45 g of $H_2O$ was added thereto dropwise at a dropping temperature of 78.3 to 80.2° C. for one hour to synthesize a 5,5'-bi-1H-tetrazolediammonium salt ($BHT.2NH_3$) by the reaction of the 5,5'-bi-1H-tetrazoledisodium salt (BHT.2Na) with the $NH_4Cl$. The filtrate was then cooled down to 20° C. and was crystallized. The precipitated crystals were separated by a centrifuge and were washed with 106.0 g of $H_2O$ to isolate 73.27 g of the wet 5,5'-bi-1H-tetrazolediammonium salt ($BHT.2NH_3$). By effecting the drying in a vacuum drier at a drying temperature of 50° C. for 8 hours, there was obtained 64.43 g of the 5,5'-bi-1H-tetrazolediammonium salt ($BHT.2NH_3$) (pale bluish white). The sum of the separated mother liquor and the washing solution was 945.9 g.

{Yield and analytical values of the 5,5'-bi-1H-tetrazolediammonium salt ($BHT.2NH_3$)]

Yield of crystals: 76.07%

Analytical values of crystals: content with $HClO_4$ tit., 99.77% copper content, 59.1 ppm

Example 2

Synthesis of the 5,5'-bi-1H-tetrazolediammonium salt ($BHT.2NH_3$)

101.68 Grams (2.00 mols) of 96.4% NaCN, 143.46 g (2.20 mols) of 99.7% $NaN_3$, and 460.2 g of water were fed into a 2-liter flask and were cooled down to a temperature of not higher than 10° C. Then, 204.9 g (2.00 mols) of 35.6% HCl was added dropwise to the slurry aqueous solution at a dropping temperature of 5.3 to 8.8° C. over a dropping time of 55 minutes to neutralize the NaCN slurry solution. A mixture aqueous solution containing 5.01 g (0.02 mols) of 99.5% $CuSO_4.5H_2O$/20.07 g of $H_2O$ was added to the homogeneous solution that has been neutralized. Next, a mixture solution of 106.10 g (1.08 mols) of a 34.6% $H_2O_2$ aqueous solution and 12.09 g (0.20 mols) of 99.7% acetic acid was added thereto dropwise at a dropping temperature of −4.2 to 11.6° C. over a dropping time of one hour and 25 minutes. A green reaction solution (pH=6) after the starting materials have been added thereto dropwise was stirred at 21.5° C. for 20 minutes and was then heated up to 39.8° C. over 45 minutes. The reaction was conducted at a temperature of 39.8 to 42.9° C. for 2 hours with stirring while being heated to synthesize chiefly a 5-cyano-1H-tetrazolesodium salt [CHT.Na] intermediate product. Thereafter, the temperature was raised from 45.3° C. to 90° C. over 35 minutes, and the reaction was conducted at a temperature of 87.0 to 90.2° C. for 2 hours, and was further conducted in a heated and refluxing manner (100.0 to 106.6° C.) for 5 hours to transform the 5-cyano-1H-tetrazolesodium salt [CHT.Na] intermediate product into a 5,5'-bi-1H-tetrazoledisodium salt [BHT.2Na]. The HPLC analysis of the reaction solution showed 97.53% of the 5,5'-bi-1H-tetrazole [BHT] and 0.31% of the 5-cyano-1H-tetrazole [CHT]. After the reaction, the reaction solution was cooled down to 80° C., the nitrogen bubbling was effected at 6 L/hour in order to decrease the HCN in the gaseous portion in the reactor down to smaller than a limit of detection. An aqueous solution of 118.87 g (2.20 mols) of 99.0% $NH_4Cl$/328.3 g of $H_2O$ was added thereto dropwise at a dropping temperature of 81.7 to 83.3° C. for one hour and 50 minutes to synthesize a 5,5'-bi-1H-tetrazolediammonium salt ($BHT.2NH_3$) by the reaction of the 5,5'-bi-1H-tetrazoledisodium salt (BHT.2Na) with the $NH_4Cl$. The filtrate was then cooled down to 9.3° C. over one hour and 45 minutes and was crystallized. The precipitated crystals were separated by a centrifuge and were washed with 199.6 g of $H_2O$ to isolate 173.28 g of the wet 5,5'-bi-1H-tetrazolediammonium salt ($BHT.2NH_3$). By effecting the drying in a vacuum drier at a drying temperature of 50° C. for 10 hours, there was obtained 142.04 g of the 5,5'-bi-1H-tetrazolediammonium salt ($BHT.2NH_3$) (pale bluish white). The sum of the separated mother liquor and the washing solution was 1492.35 g.

{Yield and analytical values of the coarse 5,5'-bi-1H-tetrazolediammonium salt ($BHT.2NH_3$)]

Yield of coarse crystals: 80.00%

Analytical values of coarse crystals: content with $HClO_4$ tit., 96.96%, copper content, 1821 ppm

Example 3

Refining the 5,5'-bi-1H-tetrazolediammonium salt ($BHT.2NH_3$) by Filtration 25.05 Grams (0.141 mols) of the coarse 5,5'-bi-1H-tetrazolediammonium salt [BH[].$2NH_3$] (Example 2), 11.49 g (0.284 mols) of 99% NaOH and 198.98 g of $H_2O$ were fed into a 300-ml flask and were heated at 40° C. to transform the 5,5'-bi-1H-tetrazolediammonium salt ($BHT.2NH_3$) into a 5,5'-bi-1H-tetrazoledisodium salt (BHT.2Na) so that coarse crystals thereof were dissolved. After the coarse crystals have been dissolved, 242.49 g of a blue filtrate from which 0.41 g of a blue insoluble component of $BHT.Cu.NH_3$ complex has been removed by hot-filtration, was heated at 80° C., and an aqueous solution of 16.74 g (0.310 mols) of 99.0% $NH_4Cl$/45.28 g of $H_2O$ was added thereto dropwise at a dropping temperature of 79.9 to 81.7° C. for one hour and 5 minutes to synthesize a 5,5'-bi-1H-tetrazolediammonium salt ($BHT.2NH_3$) by the reaction of the 5,5'-bi-1H-tetrazoledisodium salt (BHT.2Na) with the $NH_4Cl$. The filtrate was then cooled down to 8.3° C. and was crystallized. The precipitated crystals were washed with 32.6 g of $H_2O$ to isolate 29.36 g of the wet 5,5'-bi-1H-tetrazolediammonium salt ($BHT.2NH_3$). By effecting the drying in a vacuum drier at a drying temperature of 50° C. for 10 hours, there was obtained 22.66 g of the 5,5'-bi-1H-tetrazolediammonium salt ($BHT.2NH_3$).

{Yield and analytical values of the refined 5,5'-bi-1H-tetrazolediammonium salt ($BHT.2NH_3$)]

Yield of refined crystals: 91.81%

Analytical values of refined crystals: content with HclO4 tit., 98.42%, copper content, 180 ppm

Example 4

Refining the 5,5'-bi-1H-tetrazolediammonium salt ($BHT.2NH_3$) With a Chelating Resin 75.05 Grams (0.423 mols) of the coarse 5,5'-bi-1H-tetrazolediammonium salt [$BHT.2NH_3$] (Example 2), 34.52 g (0.854 mols) of 99% NaOH and 600.00 g of $H_2O$ were fed into a 1-litter flask and were heated at 40° C. to transform the 5,5'-bi-1H-tetrazolediammonium salt (BHT.2NH$_3$) into a 5,5'-bi-1H-tetrazoledisodium salt (BHT.2Na) so that coarse crystals thereof were dissolved. After the coarse crystals have been dissolved, 791.72 g of a blue filtrate from which 1.24 g of a blue insoluble component of BHT.Cu.NH$_3$ complex has been removed by hot-filtration, was divided into three to conduct the experiment of refining.

263.62 Grams of the blue filtrate divided into one-third was passed through a 135 mm×30 mm (diameter) glass column filled with 100 ml of a polyamine type chelating resin (CR-20) (produced by Mitsubishi Chemical Co.) corresponding to 55 times as large amount as the copper component in the coarse crystals that were fed, over a time of 2 hours and 30 minutes to obtain 366.7 g of the treated solution. The solution treated with the chelating resin was heated at 80° C., and an aqueous solution of 16.74 g (0.310 mols) of 99.0% NH$_4$Cl/44.97 g of H$_2$O was added thereto dropwise at a dropping temperature of 78.7 to 80.8° C. over a time of 50 minutes to synthesize a 5,5'-bi-1H-tetrazolediammonium salt (BHT.2NH$_3$) by the reaction of the 5,5'-bi-1H-tetrazoledisodium salt (BHT.2Na) with the NH$_4$Cl. The filtrate was then cooled down to 9.6° C. and was crystallized. The precipitated crystals were filtered and washed with 31.6 g of H$_2$O to isolate 25.35 g of the wet 5,5'-bi-1H-tetrazolediammonium salt (BHT.2NH$_3$). By effecting the drying in a vacuum drier at a drying temperature of 50° C. for 10 hours, there was obtained 21.37 g of the 5,5'-bi-1H-tetrazolediammonium salt (BHT.2NH$_3$) (white). {Yield and analytical values of the refined 5,5'-bi-1H-tetrazolediammonium salt (BHT.2NH$_3$)]

Yield of refined crystals: 86.38%

Analytical values of refined crystals: content with HClO$_4$ tit., 98.95%, copper content, 1.1 ppm Example 5

Refining the 5,5'-bi-1H-tetrazolediammonium salt (BHT.2NH$_3$) With a Chelating Resin 263.61 Grams of the blue filtrate of Example 4 was passed through a 34 mm×20 mm (diameter) glass column filled with 10 ml of an iminodiacetic acid type chelating resin (CR-11) (produced by Mitsubishi Chemical Co.) corresponding to 7 times as large amount as the copper component in the coarse crystals that were fed, over a time of 2 hours and 30 minutes to obtain 289.92 g of the treated solution. The solution treated with the chelating resin was heated at 80° C., and an aqueous solution of 16.75 g (0.310 mols) of 99.0% NH$_4$Cl/45.40 g of H$_2$O was added thereto dropwise at a dropping temperature of 78.7 to 80.8° C. over a time of 50 minutes to synthesize a 5,5'-bi-1H-tetrazolediammonium salt (BHT.2NH$_3$) by the reaction of the 5,5'-bi-1H-tetrazoledisodium salt (BHT.2Na) with the NH$_4$Cl. The filtrate was then cooled down to 7.0° C. over 2 hours and 30 minutes and was crystallized. The precipitated crystals were filtered and washed with 29.82 g of H$_2$O to isolate 29.11 g of the wet 5,5'-bi-1H-tetrazolediammonium salt (BHT.2NH$_3$). By effecting the drying in a vacuum drier at a drying temperature of 50° C. for 10 hours, there was obtained 22.36 g of the 5,5'-bi-1H-tetrazolediammonium salt (BHT.2NH$_3$).
{Yield and analytical values of the refined 5,5'-bi-1H-tetrazolediammonium salt (BHT.2NH$_3$)]

Yield of refined crystals: 92.32%

Analytical values of refined crystals: content with HClO$_4$ tit., 101.07%, copper content, 9.5 ppm Example 6

Synthesis of the 5,5'-bi-1H-tetrazolediammonium salt (BHT.2NH$_3$) and Refined the Reaction Solution with a Chelating Resin 1000.6 Grams (20.00 mols) of 98.0% NaCN, 1304.1 g (20.00 mols) of 99.7% NaN$_3$, and 5847.8 g of water were fed into a 20-liter flask and were cooled down to a temperature of not higher than 10° C. to form a homogeneous aqueous solution. Then, 2265.9 g (22.00 mols) of 35.4% HCl was added dropwise thereto at a dropping temperature of 0 to 8.6° C. over a dropping time of one hour and 40 minutes to neutralize the NaCN aqueous solution. An aqueous solution containing 25.09 g (0.10 mols) of 99.5% CuSO$_4$.5H$_2$O/ 113.3 g of H$_2$O was added thereto at a dropping temperature of 7.6 to 7.3° C. Next, 1179.7 g (12.00 mols) of a 34.6% H$_2$O$_2$ aqueous solution was added thereto dropwise at a dropping temperature of 5.1 to 27.4° C. over a dropping time of 2.5 hours. A green reaction solution after the starting materials have been added thereto dropwise was heated up to 40° C. over 40 minutes. The reaction was conducted at a temperature of 38.5 to 41.8° C. for 2 hours with stirring while being heated to synthesize chiefly a 5-cyano-1H-tetrazolesodium salt [CHT.Na] intermediate product. Thereafter, the temperature was raised to 90° C. over one hour, and the reaction was conducted at a temperature of 89.5 to 91.3° C. for 2 hours, and was further conducted in a heated and refluxing manner (96.7 to 102.1° C.) for 5 hours to transform the 5-cyano-1H-tetrazolesodium salt [CHT.Na] intermediate product into a 5,5'-bi-1H-tetrazoledisodium salt [BHT.2Na]. The HPLC analysis of the reaction solution showed 96.72% of the 5,5'-bi-1H-tetrazole [BHT] and 0.81% of the 5-cyano-1H-tetrazole [CHT]. To 5.82 kg of the reaction solution obtained by dividing 11.62 kg of the obtained reaction solution into one-half, there was added dropwise 25.9 g (0.405 mols) of 26.6% aqueous NH$_3$ which was 8 times as large as the amount of CuSO$_4$.5H$_2$O that was fed at a dropping temperature of 66° C. for a time of 5 minutes. Then, the reaction solution was stirred at a temperature of 68.5 to 64.8° C. for one hour to precipitate the blue insoluble component of the BHT.Cu.NH$_3$ from the green reaction solution. After the addition of 1412.1 g of diluting water, the insoluble component was removed by filtration from the reaction solution containing the insoluble component at 50° C., and was washed with 400.2 g of washing water. The total amount of the filtrate inclusive of the washing solution was 7.52 kg, and the copper content was 6.0 ppm. The amount of the blue insoluble component of the BHT.Cu.NH$_3$ separated by filtration was 11.9 g. The filtrate was passed through a 300 mm×40 mm (diameter) glass column filled with 375 ml (0.15 mols) of the chelating resin (CR-20) corresponding to three times as much as the amount of CuSO$_4$ that was fed at a temperature of 50° C. over a time of 2 hours and 30 minutes at a flow velocity (SV) of 10 to obtain 7398.7 g of the treated solution, Cu<1 ppm. 3684.7 Grams of the divided and treated solution was heated at 40° C., and an aqueous solution of 297.23 g (5.501 mols) of 99.0% NH$_4$Cl/835.0 g of H$_2$O was added thereto dropwise at a dropping temperature of 42.6 to 44.0° C. over a time of 33 minutes to synthesize a 5,5'-bi-1H-tetrazolediammonium salt (BHT.2NH$_3$) by the reaction of the 5,5'-bi-1H-tetrazoledisodium salt (BHT.2Na) with the NH$_4$Cl. The filtrate was then cooled down to 19.3° C. and was crystallized. The precipitated crystals were separated by a centrifuge and washed with 160.0 g of H$_2$O to isolate 538.33 g of the wet 5,5'-bi-1H-tetrazolediammonium salt (BHT.2NH$_3$). By effecting the drying in a hot-air drier at a drying temperature of 70° C. for 48 hours, there was obtained 354.59 g of the 5,5'-bi-1H-tetrazolediammonium salt (BHT.2NH$_3$) (white). The total amount of the separated mother liquor and the washing solution was 4408.8 g
{Yield and analytical values of the 5,5'-bi-1H-tetrazolediammonium salt (BHT.2NH$_3$)]

Yield of crystals: 79.67%

Analytical values of crystals: content with HclO$_4$ tit., 96.70%, copper content, 4.9 ppm

Example 7

Synthesis and Refining of the 5,5'-bi-1H-tetrazolediammonium salt (BHT.2NH$_3$)

1475.1 Grams (29.00 mols) of 96.4% NaCN, 2082.0 g (31.92 mols) of 99.7% NaN$_3$, and 6671.0 g of water were fed into a 20-liter glass flask and were cooled down to a temperature of not higher than 10° C. Then, 2953.5 g (29.00 mols) of 35.8% HCl was added dropwise to the slurry aqueous solution at a dropping temperature of 3.8 to 14.9° C. over a dropping time of one hour and 15 minutes to neutralize the NaCN slurry solution. A mixture aqueous solution containing 72.6 g (0.29 mols) of 99.5% CuSO$_4$.5H$_2$O/331.3 g of H$_2$O was added to the homogeneous solution that has been neutralized. Next, a mixture solution of 1539.3 g (15.66 mols) of a 34.6% H$_2$O$_2$ aqueous solution and 174.8 g (2.90 mols) of 99.7% acetic acid was added thereto dropwise at a dropping temperature of 12.8 to 30.2° C. over a dropping time of 2 hours and 15 minutes. A green reaction solution (pH=6) after the starting materials have been added thereto dropwise was stirred at 27.3° C. for 5 minutes and was then heated up to 40° C. over 45 minutes. The reaction was conducted at a temperature of 40 to 40.8° C. for 2 hours with stirring while being heated to synthesize chiefly a 5-cyano-1H-tetrazolesodium salt [CHT.Na] intermediate product. Thereafter, the temperature was raised to 40.8→90° C. over 55 minutes. and the reaction was conducted at a temperature of 90° C. for 2 hours, and was further conducted in a heated and refluxing manner (102.7 to 104.3° C.) for 2 hours and 15 minutes to transform the 5-cyano-1H-tetrazolesodium salt [CHT.Na] intermediate product into a 5,5'-bi-1H-tetrazoledisodium salt [BHT.2Na]. The HPLC analysis of the reaction solution showed 97.28% of the 5,5'-bi-1H-tetrazole [BHT] and 0.49% of the 5-cyano-1H-tetrazole [CHT]. After the reaction, the reaction solution was cooled down to 80° C. over 45 minutes, the nitrogen bubbling was effected at 60 L/hour in order to decrease the HCN in the gaseous portion in the reactor down to 30 ppm. The reaction solution was diluted by the addition of 6000 g of H$_2$O and was heated up to 66.5° C. to dissolve part of the precipitated 5,5'-bi-1H-tetrazoledisodium salt [BHT.2Na]. After dissolved, 21.04 kg of the filtrate from which 50.05 g of the white insoluble component has been removed by hot-filtration was passed through a 1300 mm×65 mm (diameter) vinyl chloride (4.3-liter) column filled with 3.6 liters of the chelating resin (CR-20) corresponding to 5 times as much as the amount of the copper component in the coarse crystals that were fed at a flow velocity (SV) of 1.56 to obtain 22.86 kg of a colorless and transparent treated solution. The solution treated with the chelating resin was heated at 80° C., and an aqueous solution of 1723.6 g (31.90 mols) of 99.0% NH$_4$Cl/4640.0 g of H$_2$O was added thereto dropwise at a dropping temperature of 80.1 to 77.3° C. over a time of one hour and as stirred at 60.0 to 78.6° C. for 3 hours to synthesize a 5,5'-bi-1H-tetrazolediammonium salt (BHT.2NH$_3$) by the reaction of the 5,5'-bi-1H-tetrazoledisodium salt (BHT.2Na) with the NH$_4$Cl. The filtrate was then cooled down to 8° C. over 19 hours and was crystallized. The precipitated crystals were separated by a centrifuge and washed with 1500.0 g of H$_2$O to isolate 2243.4 g of the wet 5,5'-bi-1H-tetrazolediammonium salt (BHT.2NH$_3$). By effecting the drying in a hot-air drier at a drying temperature of 60° C. for 23 hours, there was obtained 1952.4 g of the 5,5'-bi-1H-tetrazolediammonium salt (BHT.2NH$_3$) (pale bluish white). The total amount of the separated mother liquor and the washing solution was 28.12 kg {Yield and analytical values of the 5,5'-bi-1H-tetrazolediammonium salt (BHT.2NH$_3$)]

Yield of crystals: 78.12% based on NaCN

Analytical values of crystals: content with HClO$_4$ tit., 99.88%, copper content, 76.7 ppm

Example 8

Refining the 5,5'-bi-1H-tetrazolediammonium salt (BHT.2NH$_3$) by Filtration 391.7 Grams (6.01 mols) of 99.7% NaN$_3$, 300.5 g (6.01 mols) of 98.0% NaCN, and 1742.5 g of water were fed into a 5-liter flask and were cooled down to a temperature of not higher than 10° C. to form a homogeneous aqueous solution. Then, 681.6 g (6.60 mols) of 35.3% HCl was added dropwise thereto at a dropping temperature of 6.9 to 18.2° C. over a dropping time of 55 minutes to neutralize the NaCN aqueous solution. An aqueous solution containing 7.53 g (0.030 mols) of 99.5% CuSO$_4$.5H$_2$O/34.23 g of H$_2$O was added thereto. Next, 333.7 g (3.45 mols) of a 35.2% H$_2$O$_2$ aqueous solution was added thereto dropwise at a dropping temperature of 16.8 to 41.0° C. over a dropping time of one hour and 15 minutes. A green reaction solution after the starting materials have been added thereto dropwise was reacted at 40.7 to 41.0° C. for 2 hours with stirring while being heated to synthesize chiefly a 5-cyano-1H-tetrazolesodium salt [CHT.Na] intermediate product. Thereafter, the temperature was raised to 90° C. over 40 minutes, and the reaction was conducted at a temperature of 89.1 to 92.4° C. for 2 hours, and was further conducted in a heated and refluxing manner (100.0 to 105.8° C.) for 5 hours. The HPLC analysis of the reaction solution showed 95.37% of the 5,5'-bi-1H-tetrazole [BHT] and 0.81% of the 5-cyano-1H-tetrazole [CHT]. The reaction solution was cooled down to room temperature to obtain 3.47 kg of the reaction solution containing a 5,5'-bi-1H-tetrazoledisodium salt. 1152.1 Grams of the reaction solution divided into one-third was heated at 50° C., 3.9 g (0.040 mols) of a 35.2% H$_2$O$_2$ aqueous solution as added thereto dropwise at a dropping temperature of 53.5 to 54.0° C. over one minute and, then, 6.0 g (0.087 mols) [9 equivalents to CuSO$_4$ that was fed] of a 24.7% NH$_3$ water was added thereto followed by stirring at 52.0 to 58.0° C. for 2 hours to precipitate a blue insoluble component of the BHT.Cu.NH$_3$. After diluted with 199.5 g of H$_2$O, the reaction solution was filtered at 50° C., washed with 30.6 g of H$_2$O to separate the insoluble component, thereby to obtain 1354.4 g of the filtrate. The copper content in the filtrate was 4.0 ppm. The filtrate was heated at 80° C., and an aqueous solution of 118.9 g (2.20 mols) of 99.0% NH$_4$Cl/352.0 g of H$_2$O was added thereto dropwise at a dropping temperature of 77.6 to 82.2° C. over a time of 2 hours and 20 minutes to synthesize a 5,5'-bi-1H-tetrazolediammonium salt (BHT.2NH$_3$) by the reaction of the 5,5'-bi-1H-tetrazoledisodium salt (BHT.2Na) with the NH$_4$Cl. The filtrate was then cooled down to 18.3° C. and was crystallized. The precipitated crystals were separated by a centrifuge and washed with 136.2 g of H$_2$O to isolate 150.01 g of the wet 5,5'-bi-1H-tetrazolediammonium salt (BHT.2NH$_3$). By effecting the drying in a vacuum drier at a drying temperature of 50° C. for 8 hours, there was obtained 134.52 g of the 5,5'-bi-1H-tetrazolediammonium salt (BHT.2NH$_3$) (pale bluish white). The total amount of the separated mother liquor and the washing solution was 1764.3 g.

{Yield and analytical values of the 5,5'-bi-1H-tetrazolediammonium salt (BHT.2NH$_3$)]

Yield of crystals: 77.65%

Analytical values of crystals: content with HClO$_4$ tit., 99.37%, copper content, 33.4 ppm Example 9

Refining the 5,5'-bi-1H-tetrazolediammonium salt (BHT.2NH$_3$) by Filtration 163.0 Grams (2.50 mols) of 99.7% NaN$_3$ and 500.0 g of water were fed into a 2-liter flask and were cooled down to a temperature of not higher than 10° C. to form a homogeneous aqueous solution. Then, 3.14 g (0.0125 mols) of 99.5% CuSO$_4$.5H$_2$O and 68.5 g (2.50 mols) of 98.6% HCN were added thereto in this order. Next, 25.8 g (0.250 mols) of 35.4% HCl was added dropwise thereto at a dropping temperature of −4.6 to −2.2° C. over a dropping time of 4 minutes to adjust the pH and, then, 136.1 g (1.50 mols) of a 35.3% H$_2$O$_2$ aqueous solution was added thereto dropwise at a dropping temperature of −0.4 to 41.0° C. over a dropping time of 47 minutes. A green reaction solution after the starting materials have been added thereto dropwise was reacted at 39.0 to 41.7° C. for 2 hours with stirring while being heated to synthesize chiefly a 5-cyano-1H-tetrazolesodium salt [CHT.Na] intermediate product. Thereafter, the temperature was raised to 90° C. over 40 minutes, and the reaction was conducted at a temperature of 88.0 to 90.9° C. for 2 hours, and was further conducted in a heated and refluxing manner (100.0 to 103.8° C.) for 5 hours. The HPLC analysis of the reaction solution showed 97.11% of the 5,5'-bi-1H-tetrazole [BHT] and 0.80% of the 5-cyano-1H-tetrazole [CHT]. The reaction solution was cooled down to room temperature to obtain 892 g of the reaction solution containing a 5,5'-bi-1H-tetrazoledisodium salt. 446.0 Grams of the reaction solution divided into one-half was heated at 50° C., 5.7 g (0.063 mols) of a 35.3% H$_2$O$_2$ aqueous solution was added thereto dropwise at a dropping temperature of 53.0° C. over one minute and, then, the reaction was conducted at 52.4 to 54.8° C. for one hour with stirring while being heated. Next, 3.4 g (0.050 mols) [8 equivalents to CuSO$_4$ that was fed] of a 24.9% aqueous NH$_3$ was added thereto, and the reaction solution was stirred at 51.0 to 53.1° C. for 2 hours to precipitate a blue insoluble component of the BHT.Cu.NH$_3$. The insoluble component was hot-filtered at 50° C., washed with 26.8 g of H$_2$O and was separated thereby to obtain 525.3 g of the filtrate which contained 2.3 ppm of copper component. The filtrate was heated at 80° C., and an aqueous solution of 74.3 g (1.38 mols) of 99.0% NH$_4$Cl/220.8 g of H$_2$O was added thereto dropwise at a dropping temperature of 78.5 to 81.1° C. over a time of 2 hours to synthesize a 5,5'-bi-1H-tetrazolediammonium salt (BHT.2NH$_3$) by the reaction of the 5,5'-bi-1H-tetrazoledisodium salt (BHT.2Na) with the NH$_4$Cl. The filtrate was then cooled down to 18.3° C. and was crystallized. The precipitated crystals were separated by a centrifuge and washed with 100.0 g of H$_2$O to isolate 94.10 g of the wet 5,5'-bi-1H-tetrazolediammonium salt (BHT.2NH$_3$). By effecting the drying in a vacuum drier at a drying temperature of 50° C. for 8 hours, there was obtained 87.03 g of the 5,5'-bi-1H-tetrazolediammonium salt (BHT.2NH$_3$) (white). The total amount of the separated mother liquor and the washing solution was 1189.1 g.

{Yield and analytical values of the 5,5'-bi-1H-tetrazolediammonium salt (BHT.2NH$_3$)]

Yield of crystals: 80.50%

Analytical values of crystals: content with HClO$_4$ tit., 99.52%, copper content, 5.0 ppm Example 10

Refining the 5,5'-bi-1H-tetrazolediammonium salt (BHT.2NH$_3$) with a Chelating Resin 50.1 Grams (0.290 mols) of the coarse 5,5'-bi-1H-tetrazolediammonium salt [BHT.2NH$_3$] (Example 1), 23.7 g (11.66 mols) of 99% NaOH and 344 g of H$_2$O were fed into a 500-mL flask and were heated at 50° C. with stirring to transform the 5,5'-bi-1H-tetrazolediammonium salt (BHT.2NH$_3$) into a 5,5'-bi-1H-tetrazoledisodium salt (BHT.2Na) so that coarse crystals thereof were dissolved. The blue solution (Cu, 6.8 ppm) was passed through a 300 mm×20 mm (diameter) glass column filled with 12 ml of a reproduced chelating resin (CR-20) (produced by Mitsubishi Kagaku Co.) corresponding to 100 times as large amount as the copper component in the coarse crystals that were fed, at a temperature of 50° C. over a time of 3 hours at a flow velocity (SV) of 10 to obtain 434.9 g of a colorless transparent treated solution. The solution treated with the chelating resin was heated at 80° C., and an aqueous solution of 34.52 g (0.6389 mols) of 99.0% NH$_4$Cl/45.20 g of H$_2$O was added thereto dropwise at a dropping temperature of 78.8 to 80.1° C. over a time of one hour to synthesize a 5,5'-bi-1H-tetrazolediammonium salt (BHT.2NH$_3$) by the reaction of the 5,5'-bi-1H-tetrazoledisodium salt (BHT.2Na) with the NH$_4$Cl. The solution was then cooled down to 5.3° C. and was crystallized. The precipitated crystals were separated by a centrifuge and washed with 37.0 g of H$_2$O to isolate 53.37 g of the wet 5,5'-bi-1H-tetrazolediammonium salt (BHT.2NH$_3$). By effecting the drying in a vacuum drier at a drying temperature of 50° C. for 7 hours, there was obtained 45.73 g of the 5,5'-bi-1H-tetrazolediammonium salt (BHT.2NH$_3$) (white). The total amount of the separated mother liquor and the washing solution was 511.5 g.

{Yield and analytical values of the refined 5,5'-bi-1H-tetrazolediammonium salt (BHT.2NH$_3$)]

Yield of refined crystals: 90.98%

Analytical values of refined crystals: content with HClO$_4$ tit., 99.32%, copper component<1 ppm Example 11

Synthesis of the 5,5'-bi-1H-tetrazolediammonium salt (BHT.2NH$_3$)

1474.7 Grams (29.00 mols) of 96.4% NaCN, 2080.4 g (31.90 mols) of 99.7% NaN$_3$, and 6670.0 g of water were fed into a 20-liter glass flask and were cooled down to a temperature of not higher than 10° C. Then, 2954.5 g (29.00 mols) of 35.8% HCl was added dropwise to the slurry aqueous solution at a dropping temperature of 0.5 to 7.1° C. over a dropping time of one hour and 20 minutes to neutralize the NaCN slurry solution. A mixture aqueous solution containing 72.6 g (0.29 mols) of 99.5% CuSO$_4$.5H$_2$O/332.7 g of H$_2$O was added to the homogeneous solution that has been neutralized. Next, a mixture solution of 1540.5 g (15.66 mols) of a 34.6% H$_2$O$_2$ aqueous solution and 174.7 g (2.90 mols) of 99.7% acetic acid was added thereto dropwise at a dropping temperature of 4.7 to 20.5° C. over a dropping time of 4 hours and 25 minutes. A green reaction solution (pH=6) after the starting materials have been added thereto dropwise was stirred at 14.5° C. for 25 minutes and was then heated up to 39.8° C. over 65 minutes. The reaction was conducted at a temperature of 40 to 45.3° C. for 2 hours with stirring while being heated to synthesize chiefly a 5-cyano-1H-tetrazolesodium salt [CHT.Na] intermediate product. Thereafter, the temperature was raised to 45.3→90° C. over 55 minutes, and the reaction was conducted at a temperature of 90° C. for one hour, and was further conducted in a heated and refluxing manner (100.0 to 107.2° C.) for 4 hours and 30 minutes to transform the 5-cyano-1H-tetrazolesodium salt [CHT.Na] intermediate product into a 5,5'-bi-1H-tetrazoledisodium salt [BHT.2Na]. The HPLC analysis of the reaction solution showed 98.14% of the 5,5'-bi-1H-tetrazole [BHT] but the amount of the 5-cyano-1H-tetrazole [CHT] was smaller than a detectable limit. After the reaction, the reaction solution was cooled down to 80° C. over 45 minutes, the nitrogen bubbling was effected at 60 L/hour in order to decrease the HCN in the gaseous portion in the reactor down to 15 ppm. An aqueous solution of 1724.4 g (31.90 mols) of 99.0% $NH_4Cl$/4840.8 g of $H_2O$ was added thereto dropwise at a dropping temperature of 80.2 to 76.3° C. over a time of one hour and 35 minutes to synthesize a 5,5'-bi-1H-tetrazolediammonium salt (BHT.2NH$_3$) by the reaction of the 5,5'-bi-1H-tetrazoledisodium salt (BHT.2Na) with the $NH_4Cl$. The reaction solution was then cooled down to 9° C. over 13 hours and 40 minutes and was crystallized. The precipitated crystals were separated by a centrifuge and washed with 1500.0 g of $H_2O$ to isolate 2283.0 g of the wet 5,5'-bi-1H-tetrazolediammonium salt (BHT.2NH$_3$). By effecting the drying in a hot-air drier at a drying temperature of 60° C. for 21 hours, there was obtained 2120.6 g of the 5,5'-bi-1H-tetrazolediammonium salt (BHT.2NH$_3$) (pale bluish white). The total amount of the separated mother liquor and the washing solution was 20.57 kg.

{Yield and analytical values of the coarse 5,5'-bi-1H-tetrazolediammonium salt (BHT.2NH$_3$)}

Yield of coarse crystals: 81.16% based on NaCN

Analytical values of coarse crystals: content with $HClO_4$ tit., 95.54%, copper content, 2411.2 ppm Analytical value of separated mother liquor+washing solution: Cu, 123.9 ppm Example 12

Refining the 5,5'-bi-1H-tetrazolediammonium salt (BHT.2NH$_3$) With a Chelating Resin 2020 Grams (11.21 mols) of the coarse 5,5'-bi-1H-tetrazolediammonium salt [BHT.2NH$_3$] (Example 11), 915 g (22.64 mols) of 99% NaOH and 14000 g of $H_2O$ were fed into a 20-liter glass flask and were heated at 20→50° C. to transform the 5,5'-bi-1H-tetrazolediammonium salt (BHT.2NH$_3$) into a 5,5'-bi-1H-tetrazoledisodium salt (BHT.2Na) so that coarse crystals thereof were dissolved. After the coarse crystals have been dissolved, 16.94 kg of a blue filtrate obtained by removing 55.43 g of a blue insoluble component of the BHT.Cu.NH$_3$ from the solution by hot-filtration was passed through a 600 mm×65 mm (diameter) vinyl chloride (2.0-liter) column filled with 1.6 liters of the polyamine type chelating resin (CR-20) (produced by Mitsubishi Chemical Co.) corresponding to 8.5 times as large amount as the copper component in the coarse crystals that were fed, at a flow velocity (SV) of 3.14 to obtain 17.50 kg of a colorless transparent treated solution, copper component<1 ppm. The solution treated with the chelating resin was heated at 80° C., and an aqueous solution of 1332.5 g (24.66 mols) of 99.0% $NH_4Cl$/3570.0 g of $H_2O$ was added thereto dropwise at a dropping temperature of 78.0 to 79.9° C. over a time of 50 minutes to synthesize a 5,5'-bi-1H-tetrazolediammonium salt (BHT.2NH$_3$) by the reaction of the 5,5'-bi-1H-tetrazoledisodium salt (BHT.2Na) with the $NH_4Cl$. The solution was then cooled down to 5.5° C. over 15 hours and was crystallized. The precipitated crystals were separated by a centrifuge and washed with 1500.0 g of $H_2O$ to isolate 1919.6 g of the wet 5,5'-bi-1H-tetrazolediammonium salt (BHT.2NH$_3$). By effecting the drying in a hot-air drier at a drying temperature of 60° C. for 21 hours, there was obtained 1839.9 g of the 5,5'-bi-1H-tetrazolediammonium salt (BHT.2NH$_3$) (white). The total amount of the separated mother liquor and the washing solution was 21.78 kg.

{Yield and analytical values of the refined 5,5'-bi-1H-tetrazolediammonium salt (BHT.2NH$_3$)}

Yield of refined crystals: 94.74%

Analytical values of refined crystals: content with $HclO4$ tit., 99.37%, copper content, 1.3 ppm Example 13

Synthesis of the 5,5'-bi-1H-tetrazolediammonium salt (BHT.2NH$_3$)

1000.6 Grams (20.00 mols) of 97.96% NaCN, 1304.1 g (20.00 mols) of 99.70% NaN$_3$, and 5845.2 g of water were fed into a 20-liter glass flask and were cooled down to a temperature of not higher than 10° C. to form a homogeneous aqueous solution. Then, 2265.2 g (22.00 mols) of 35.4% HCl was added dropwise thereto at a dropping temperature of 0 to 8.6° C. over a dropping time of one hour and 40 minutes to neutralize the NaCN aqueous solution. An aqueous solution containing 25.09 g (0.10 mols) of 99.5% $CuSO_4.5H_2O$/113.30 g of $H_2O$ was added thereto at a dropping temperature of 7.6 to 7.3° C. Next, 1179.7 g (12.00 mols) of a 34.6% $H_2O_2$ aqueous solution was added thereto dropwise at a dropping temperature of 5.1 to 27.4° C. over a dropping time of 2 hours and 30 minutes. A green reaction solution after the starting materials have been added thereto dropwise was heated up to 40° C. over 35 minutes. The reaction was conducted at a temperature of 38.5 to 41.8° C. for 2 hours with stirring while being heated to synthesize chiefly a 5-cyano-1H-tetrazolesodium salt [CHT.Na] intermediate product. Thereafter, the temperature was raised to 90° C. over 55 minutes, and the reaction was conducted at a temperature of 89.5 to 91.3° C. for 2 hours, and was further conducted in a heated and refluxing manner (96.7 to 102.1° C.) for 5 hours to transform the 5-cyano-1H-tetrazolesodium salt [CHT.Na] intermediate product into a 5,5'-bi-1H-tetrazoledisodium salt [BHT.2Na]. The HPLC analysis of the reaction solution showed 96.72% of the 5,5'-bi-1H-tetrazole [BHT] and 0.81% of the 5-cyano-1H-tetrazole [CHT]. The amount of the obtained reaction solution was 11.62 kg. 5780 Grams of the reaction solution [NaCN (9.948 mols) base] divided into one-half was heated at 80° C., and an aqueous solution of 594.3 g (11,00 mols) of 99.0% $NH_4Cl$/1669.7 g of $H_2O$ was added thereto dropwise at a dropping temperature of 79.7 to 81.3° C. over a time of 35 minutes to synthesize a 5,5'-bi-1H-tetrazolediammonium salt (BHT.2NH$_3$) by the reaction of the 5,5'-bi-1H-tetrazoledisodium salt (BHT.2Na) with the $NH_4Cl$. The reaction solution was the cooled down to 20.2° C. over 3 hours and 25 minutes and was crystallized. The precipitated crystals were separated by a centrifuge and washed with 297.2 g of $H_2O$ to isolate 761.1 g of the wet 5,5'-bi-1H-tetrazolediammonium salt (BHT.2NH$_3$). By effecting the drying in a hot-air drier at a drying temperature of 70° C. for 48 hours, there was obtained 721.47 g of the 5,5'-bi-1H-tetrazolediammonium salt (BHT.2NH$_3$) (bluish white). The total amount of the separated mother liquor and the washing solution was 7.46 kg.

{Yield and analytical values of the coarse 5,5'-bi-1H-tetrazolediammonium salt (BHT.2NH$_3$)}

Yield of coarse crystals: 78.60%

Analytical values of coarse crystals: content with $HClO_4$ tit., 93.29%, copper content, 4849 ppm Analytical value of separated mother liquor+washing solution: Cu, 1.3 ppm Example 14

Refining the 5,5'-bi-1H-tetrazolediammonium salt ($BHT.2NH_3$).

670.2 Grams (3.632 mols of the coarse 5,5'-bi-1H-tetrazolediammonium salt [$BHT.2NH_3$] of Example 13, 302.1 g (7.447 mols) of 99% NaOH and 5000 g of $H_2O$ were fed into a 10-liter flash and were heated at 50° C. to transform the 5,5'-bi-1-H-tetrazolediammonium salt ($BHT.2NH_3$) into a 5,5'-bi-1H-tetrazoledisodium salt ($BHT.2Na$) so that coarse crystals thereof were dissolved. After the coarse crystals have been dissolved, the blue insoluble component of the $BHT.Cu.NH_3$ was hot-filtered, washed with 195.2 g of washing water, and 10.58 g of the insoluble component was separated. 5950 Grams of the blue filtrate (pH=9, Cu, 2.8 ppm) was heated at 50° C. and was passed through a 300 mm×40 mm (diameter) glass column filled with 375 ml (0.15 mols) of the chelating resin (CR-20) (produced by Mitsubishi Chemical Co.) corresponding to 3 times as large amount as $CuSO_4$ in the coarse 5,5'-bi-1H-tetrazolediammonium salt [$BHT.2NH_3$] at a temperature of 50° C. for one hour and 40 minutes at a flow velocity (SV) of 10 to obtain 5970 g of a treated solution, copper content <1 ppm. 2977.2 Grams of the treated solution [$BHT.2NH_3$ (1.805 mols) base] divided into one-half was heated at 40° C., and an aqueous solution of 220.03 g (5.501 mols) of 99.0% $NH_4Cl$/620.06 g of $H_2O$ was added thereto dropwise at a dropping temperature of 43.0 to 43.8° C. over a time of 31 minutes to synthesize a 5,5'-bi-1H-tetrazolediammonium salt ($BHT.2NH_3$) by the reaction of the 5,5'-bi-1H-tetrazoledisodium salt ($BHT.2Na$) with the $NH_4Cl$. The treated solution was then cooled down to 19.7° C. over 3 hours and 50 minutes and was crystallized. The precipitated crystals were separated by a centrifuge and washed with 295.9 g of $H_2O$ to isolate 333.15 g of the wet 5,5'-bi-1H-tetrazolediammonium salt ($BHT.2NH_3$). By effecting the drying in a hot-air drier at a drying temperature of 70° C. for 24 hours, there was obtained 295.41 g of the 5,5'-bi-1H-tetrazolediammonium salt ($BHT.2NH_3$) (white). The total amount of the separated mother liquor and the washing solution was 3761.5 g.

{Yield and analytical values of the 5,5'-bi-1H-tetrazolediammonium salt ($BHT.2NH_3$)]

Yield of refined crystals: 94.88%

Analytical values of refined crystals: content with $HClO_4$ tit., 99.80%, copper content<1 ppm Example 15

Synthesis of the 5,5'-bi-1H-tetrazolediammonium salt [$BHT.2NH_3$].

130.41 Grams (2.000 mols) of 99.7% $NaN_3$, 2.51 g (0.010 mols) of 99.5% $CuSO_4.5H_2O$, and 220.0 g of water were fed into a 1-liter glass flash and were cooled down to a temperature of not higher than 0° C. to form a brown slurry solution. Then, 53.29 g (1.968 mols) of 99.48% HCN was added dropwise thereto at a dropping temperature of −4.5 to −2.0° C. over a dropping time of 12 minutes. The pH of the reaction solution after the dropwise addition was 6. By taking into consideration a change in the pH after the dropwise addition of the hydrogen peroxide water, 20.37 g (0.200 mols) of 35.8% HCL was added dropwise at a dropping temperature of −3.5 to −2.8° C. over a dropping time of 8 minutes. Next, 117.95 g (1.200 mols) of a 34.6% $H_2O_2$ aqueous solution was added thereto dropwise at a dropping temperature of −2.6 to 23.6° C. over a dropping time of 3 hours. A black reaction solution (pH=6) after the starting materials have been added thereto dropwise was stirred at room temperature for one hour and was, then, heated up to 40° C. over 45 minutes. The reaction was conducted at a temperature of 38.0 to 41.3° C. for 2 hours with stirring while being heated to synthesize chiefly a 5-cyano-1H-tetrazolesodium salt [CHT.Na] intermediate product. Hereinafter, the temperature was raised to 90° C. over 33 minutes, and the reaction was conducted at a temperature of 88.0 to 92.0° C. for 2 hours, and was further conducted in a heated and refluxing manner (101.9° C.) for 5 hours. The HPLC analysis of the reaction solution showed 98.38% of the 5,5'-bi-1H-tetrazole [BHT] and 0.62% of the 5-cyano-1H-tetrazole [CHT]. After the reaction, the reaction was cooled down to 80° C., and an aqueous solution of 118.87 g (2.200 mols) of 99.0% $NH_4Cl$/222.90 g of $H_2O$ was added thereto dropwise at a dropping temperature of 71.3 to 84.9° C. over a time of 55 minutes to synthesize a 5,5'-bi-1H-tetrazolediammonium salt ($BHT.2NH_3$) by the reaction of the 5,5'-bi-1H-tetrazoledisodium salt ($BHT.2Na$) with the $NH_4Cl$. The reaction solution was then cooled down to 20° C. and was crystallized. The precipitated crystals were separated by a centrifuge and washed with 103.1 g of $H_2O$ to isolate 172.32 g of the wet 5,5'-bi-1H-tetrazolediammonium salt ($BHT.2NH_3$). By effecting the drying in a vacuum drier at a drying temperature of 50° C. for 8 hours, there was obtained 147.05 g of the 5,5'-bi-1H-tetrazolediammonium salt ($BHT.2NH_3$) (yellowish green). The total amount of the separated mother liquor and the washing solution was 787.1 g.

{Yield and analytical values of the coarse 5,5'-bi-1H-tetrazolediammonium salt ($BHT.2NH_3$)]

Yield of coarse crystals: 83.58%

Analytical values of coarse crystals: content with $HClO_4$ tit., 97.86%, copper content, 3161.4 ppm Example 16

Refining the 5,5'-bi-1H-tetrazolediammonium salt ($BHT.2NH_3$) with a chelating resin.

100.00 Grams (0.568 mols) of the coarse 5,5'-bi-1H-tetrazolediammonium salt [$BHT.2NH_3$] (Example 15), 46.30 g (1.146 mols) of 99% NaOH and 232.49 g of $H_2O$ were fed into a 1-liter flask, heated at 60° C. and were stirred for one hour. The 5,5'-bi-1H-tetrazolediammonium salt [$BHT.2NH_3$] was transformed into a 5,5'-bi-1H-tetrazoledisodium salt ($BHT.2Na$) so that coarse crystals thereof were dissolved. After the coarse crystals have been dissolved, a blue insoluble component of the $BHT.Cu.NH_3$ was hot-filtered and was washed with 304.6 g of $H_2O$ to obtain 604.5 g of a blue filtrate. Since the blue insoluble component of the $BHT.Cu.NH_3$ has further precipitated from the separated mother liquor, the solution was hot-filtered again at a solution temperature of 50° C. to separate the insoluble component. The amount of the separated mother liquor after washed with water was 861.63 g. 444.29 Grams of the separated mother liquor condensed to about one-half was passed through a 160 mm×20 mm (diameter) glass column filled with 88.5 ml of the chelating resin (CR-20) (produced by Mitsubishi Chemical Co.) corresponding to 5 times as large amount as the copper component in the coarse crystals that were fed, at a temperature of 60° C. over 30 minutes at a flow velocity (SV) of 10 to obtain 483.21 g of a colorless transparent treated solution. 112.92 Grams of $H_2O$ was added thereto and 596.13 g of the solution treated with the chelating resin was heated at 80° C., and an aqueous solution of 67.56 g (1.250 mols) of 99.0% $NH_4Cl$/126.57 g of $H_2O$ was added thereto dropwise at a dropping temperature of 71.3 to 76.4° C. over a time of 47 minutes to synthesize a 5,5'-bi-1H-tetrazolediammonium salt ($BHT.2NH_3$) by the reaction of the 5,5'-bi-1H-tetrazoledisodium salt (BHT.2Na) with the $NH_4Cl$. The solution was then cooled down to 20° C. and was crystallized. The precipitated crystals were separated by a centrifuge and washed with 53.7 g of $H_2O$ to isolate 99.64 g of the wet 5,5'-bi-1H-tetrazolediammonium salt ($BHT.2NH_3$). By effecting the drying in a vacuum drier at a drying temperature of 50° C. for 8 hours, there was obtained 90.13 g of the 5,5'-bi-1H-tetrazolediammonium salt ($BHT.2NH_3$) (white). The total amount of the separated mother liquor and the washing solution was 732.6 g.

{Yield and analytical values of the refined 5,5'-bi-1H-tetrazolediammonium salt ($BHT.2NH_3$)]

Yield of refined crystals: 92.61%

Analytical values of refined crystals: content with $HClO_4$ tit., 99.46%, copper content, 1.8 ppm Example 17

Synthesis of the 5,5'-bi-1H-tetrazolediammonium salt ($BHT.2NH_3$).

737.3 Grams (14.50 mols) of 96.4% NaCN, 945.6 g (14.50 mols) of 99.7% $NaN_3$, and 3335.8 g of water were fed into a 10-liter flask and were cooled down to a temperature of not higher than 10° C. to form a white slurry aqueous solution. Then, 1476.8 g (14.50 mols) of 35.8% HCl was added dropwise thereto at a dropping temperature of 7.9 to 14.0° C. over a dropping time of one hour and 25 minutes to neutralize the white slurry aqueous solution thereby to adjust the pH of the reaction solution to be 5 to 6. An aqueous solution containing 36.4 g (0.145 mols) of 99.5% $CuSO_4$·$5H_2O$/180.0 g of $H_2O$ was added thereto at a dropping temperature of 7.3° C. Next, a mixture solution of 770.3 g (7.83 mols) of a 34.6% $H_2O_2$ aqueous solution and 87.2 g (1.45 mols) of 99.7% acetic acid was added thereto dropwise at a dropping temperature of 5.1 to 37.5° C. over a dropping time of one hour and 35 minutes. A green reaction solution after the starting materials have been added thereto dropwise was heated up to 40° C. over 50 minutes. The reaction was conducted at a temperature of 40.0 to 40.4° C. for 2 hours with stirring while being heated to synthesize chiefly a 5-cyano-1H-tetrazolesodium salt [CHT.Na] intermediate product. Thereafter, the temperature was raised to 90° C. over 50 minutes, and the reaction was conducted at a temperature of 87.4 to 90.1° C. for 2 hours, and was further conducted in a heated and refluxing manner (100.0 to 106.1° C.) for 4.5 hours to transform the 5-cyano-1H-tetrazolesodium salt [CHT.Na] intermediate product into a 5,5'-bi-1H-tetrazoledisodium salt [BHT.2Na]. The HPLC analysis of the reaction solution showed 96.53% of the 5,5'-bi-1H-tetrazole [BHT] and 1.25% of the 5-cyano-1H-tetrazole [CHT]. After the reaction, the reaction solution was cooled down to 80° C., and the nitrogen bubbling was effected at 30 L/hour for 2 hours to decrease the HCN in the gaseous portion in the reactor. Then, an aqueous solution of 862.5 g (15.96 mols) of 99.0% $NH_4Cl$/2521.3 g of $H_2O$ was added thereto dropwise at a dropping temperature of 77.0 to 82.4° C. over a time of one hour and 20 minutes to synthesize a 5,5'-bi-1H-tetrazolediammonium salt ($BHT.2NH_3$) by the reaction of the 5,5'-bi-1H-tetrazoledisodium salt (BHT.2Na) with the $NH_4Cl$. The reaction solution was then cooled down to 5.0° C. over 14 hours and 40 minutes and was crystallized. The precipitated crystals were separated by a centrifuge and washed with 750 g of $H_2O$ to isolate 1375.1 g of the wet 5,5'-bi-1H-tetrazolediammonium salt ($BHT.2NH_3$). By effecting the drying in a hot-air drier at a drying temperature of 60° C. for 21 hours, there was obtained 1055.1 g of the 5,5'-bi-1H-tetrazolediammonium salt ($BHT.2NH_3$) (pale bluish white). The total amount of the separated mother liquor and the washing solution was 10.14 kg.

{Yield and analytical values of the coarse 5,5'-bi-1H-tetrazolediammonium salt ($BHT.2NH_3$)]

Yield of coarse crystals: 81.77%

Analytical values of coarse crystals: content with $HClO_4$ tit., 96.73%, copper content, 3654.8 ppm Example 18

Refining the 5,5'-bi-1H-tetrazolediammonium salt ($BHT.2NH_3$) with a chelating resin.

1027.0 Grams (5.77 mols) of the coarse 5,5'-bi-1H-tetrazolediammonium salt [$BHT.2NH_3$] (Example 17), 471.0 g (11.66 mols) of 99% NaOH and 7000 g of $H_2O$ were fed into a 20-liter flask and were heated at 50° C. with stirring to transform the 5,5'-bi-1H-tetrazolediammonium salt ($BHT.2NH_3$) into a 5,5'-bi-1H-tetrazoledisodium salt (BHT.2Na) so that coarse crystals thereof were dissolved. After the coarse crystals have been dissolved, the blue insoluble component of the $BHT.Cu.NH_3$ was hot-filtered, washed with 100.0 g of $H_2O$ to obtain 8.48 kg of a blue filtrate, and 55.43 g of the insoluble component was separated. 8.48 kg of the blue filtrate (Cu, 7.4 ppm) was passed through a 600 mm×65 mm (diameter) vinyl chloride (2.0-liter) column filled with 740 ml of the regenerated chelating resin (CR-20, used twice for refining coarse crystals, and regenerated twice) corresponding to 5 times as large amount as Cu component in the coarse crystals that were fed at a temperature of 50° C. over 4 hours and 45 minutes at a flow velocity (SV) of 2.7 obtain 8.58 kg of a colorless and transparent treated solution. The solution treated with the chelating resin was heated at 80° C., and an aqueous solution of 686.0 g (12.70 mols) of 99.0% $NH_4Cl$/1840.0 g of $H_2O$ was added thereto dropwise at a dropping temperature of 80.5 to 81.1° C. over a time of 65 minutes to synthesize a 5,5'-bi-1H-tetrazolediammonium salt ($BHT.2NH_3$) by the reaction of the 5,5'-bi-1H-tetrazoledisodium salt (BHT.2Na) with the $NH_4Cl$. The treated solution was then cooled down to 8° C. and was crystallized. The precipitated crystals were separated by a centrifuge and washed with 750.0 g of $H_2O$ to isolate 957.6 g of the wet 5,5'-bi-1H-tetrazolediammonium salt ($BHT.2NH_3$). By effecting the drying in a hot-air drier at a drying temperature of 60° C. for 21 hours, there was obtained 924.2 g of the 5,5'-bi-1H-tetrazolediammonium salt ($BHT.2NH_3$) (white). The total amount of the separated mother liquor and the washing solution was 10.74 kg.

{Yield and analytical values of the refined 5,5'-bi-1H-tetrazolediammonium salt ($BHT.2NH_3$)]

Yield of refined crystals: 91.93%

Analytical values of refined crystals: content with $HClO_4$ tit., 98.80%, copper content, 1.8 ppm According to the present invention, the steps of preparing an object 5,5'-bi-1H-tetrazolediammonium salt ($BHT.2NH_3$) from the cheap and easy-to-handle starting materials are conducted based on the one-pot reaction, the aqueous hydrogen peroxide and aqueous ammonia are added to the reaction solution to remove by filtration a blue insoluble component of a copper•ammonia•5,5'-bi-1H-tetrazole complex which chiefly comprises copper that serves as the catalyst, and the reaction solution is reacted with an aqueous solution of ammonium chloride to separate the 5,5'-bi-1H-tetrazolediammonium salt crystals having a copper content of as small as 5 to 35 ppm. Further, even coarse crystals of a copper-containing 5,5'-bi-1H-tetrazolediammonium is dissolved in an aqueous solution of sodium hydroxide, and a blue insoluble component of the precipitated copper.ammonia.5,5'-bi-1H-tetrazole complex is simply separated by filtration, making it possible to easily remove not less than 90% of copper components which are impurities from the 5,5'-bi-1H-tetrazolediammonium salt crystals and from the separated mother liquor. By using the reaction solution treated with the chelating resin in combination with the solution in which the 5,5'-b-1H-tetrazolediammonium salt is dissolved, further, it is allowed to obtain highly pure crystals of 5,5'-bi-1H-tetrazolediammonium salt having a copper content of 1 to 5 ppm maintaining an yield of as high as 80%. It is thus made possible to prepare the highly pure 5,5'-bi-1H-tetrazolediammonium salt having a copper content of 1 to 5 ppm or less through a one-pot synthesizing route and a simple refining operation.

What is claimed is:

1. A process for the preparation of a highly pure 5,5'-bi-1H-tetrazolediammonium salt comprising; adding a small amount of ammonia water to a reaction solution containing a 5,5'-bi-1H-tetrazoledisodium salt synthesized in the presence of a copper catalyst, removing by filtration the blue insoluble components of formed copper.ammonia.5,5'-bi-1H-tetrazole complex to obtain a filtrate of the 5,5'-bi-1H-tetrazoledisodium salt and reacting the filtrate with an aqueous solution of ammonium chloride, and recovering the formed, highly pure ammonium salt as sparingly soluble crystals.

2. The process according to claim 1, wherein the reaction solution containing a 5,5'-bi-1H-tetrazoledisodium salt is obtained by synthesizing a dicyan by adding, as an oxidizing agent, an aqueous hydrogen peroxide to an aqueous solution of the starting materials, the pH of which is adjusted to be 5 to 7 by addition of a small amount of acidic substance, in the presence of hydrogen cyanide or sodium cyanide, sodium azide and a catalytic amount of a copper salt, followed by a heat-cyclization reaction comprising heating the reaction solution to execute the dimerization and the ring-closing by oxidation.

3. The process according to claim 1 wherein a small amount of aqueous hydrogen peroxide and a small amount of ammonia water are added to the reaction solution containing the 5,5'-bi-1H-tetrazoledisodium salt.

4. The process according to claim 2 wherein a small amount of aqueous hydrogen peroxide and a small amount of ammonia water are added to the reaction solution containing the 5,5'-bi-1H-tetrazoledisodium salt.

5. The process according to claim 1 wherein the filtrate obtained by removal of the blue insoluble components of the formed copper.ammonia.5,5'-bi-1H-tetrazole complex is further treated with a chelating resin followed by the reaction with an aqueous solution of ammonium chloride.

6. The process according to claim 5 wherein the filtrate obtained by removal of the blue insoluble components of the formed obtained by removal of teh blue insoluble components of the formed copper•ammonia•5,5'-1H-tetrazole complex is further treated with a chelating resin followed by the reaction with an aqueous solution of ammonium chloride.

7. The process according to claim 1 wherein the formed 5,5'-bi-1H-tetrazolediammonium salt, obtained by reacting the solution containing the 5,5'-bi-1H-tetrazoledisodium salt with the aqueous solution of ammonium chloride, is separated as coarse copper-containing crystals, said crystals are reacted with an aqueous solution of sodium hydroxide producing an aqueous solution of 5,5'-bi-1H-tetrazoledisodium salt which is dissolved therein, from which the blue insoluble component of copper.ammonia.5,5'-bi-1H-tetrazole complex is removed, followed by treatment with a chelating resin.

8. The process according to claim 7 wherein the formed 5,5'-bi-1H-tetrazoledisodium salt with the aqueous solution of ammonium chloride, is separated as coarse copper-containing crystals, said crystals are reacted with an aqueous solution of sodium hydroxide producing an aqueous solution of the 5,5'-bi-1H-tetrazoledisodium salt which is dissolved therein, from which the blue insoluble component of copper.ammonia.5,5'-bi-1H-tetrazole complex is removed, followed by treatment with a chelating resin.

9. The process according to claim 3 wherein the molar ratio of the aqueous hydrogen peroxide added to the aqueous solution of starting materials is increased so that the catalytic amount of copper salt migrates into the coarse 5,5'-bi-1H-tetrazolediammonium salt crystals to be separated.

10. The process according to claim 8 wherein the molar ratio of the aqueous hydrogen peroxide added to the aqueous solution of starting materials is increased so that the catalytic amount of copper salt migrates into the coarse 5,5'-bi-1H-tetrazolediammonium salt crystals to be separated.

11. The process according to claim 2 wherein the aqueous hydrogen peroxide is added to the reaction for the synthesis of the 5,5'-bi-1H-tetrazoledisodium salt in an amount such that the molar ratio (E/A) of the aqueous hydrogen peroxide (E) to the hydrogen cyanide or the sodium cyanide (A) used for the synthesis is from 0.5 to 0.8.

12. The process according to claim 10 wherein the aqueous hydrogen peroxide is added to the reaction for the synthesis of the 5,5'-bi-1H-tetrazoledisodium salt in an amount such that the molar ratio (E/A) of the aqueous hydrogen peroxide (E) to the hydrogen cyanide or the sodium cyanide (A) used for the synthesis is from 0.5 to 0.8.

13. The process according to claim 2 wherein, following the reaction of synthesizing the 5,5'-bi-1H-tetrazoledisodium salt, the aqueous hydrogen peroxide is added in such an amount that the molar ratio (H/A) of the aqueous hydrogen peroxide (H) to the hydrogen cyanide or the sodium cyanide (A) used for the synthesis is from 0.001 to 0.20.

14. The process according to claim 12 wherein, following the reaction of synthesizing the 5,5'-bi-1H- tetrazoledisodium salt, the aqueous hydrogen peroxide is added in such an amount that the molar ratio (H/A) of the aqueous hydrogen peroxide (H) to the hydrogen cyanide or the sodium cyanide (A) used for the synthesis is from 0.001 to 0.20.

15. The process according to claim 2 wherein the amount of the aqueous ammonia added to the reaction solution of 5,5'-bi-1H-tetrazoledisodium salt is such that the molar ratio (G/A) of the ammonia (G) to the hydrogen cyanide or the sodium cyanide (A) used for the synthesis is from 0.01 to 0.16.

16. The process according to claim 15 wherein the amount of the aqueous ammonia added to the reaction solution of 5,5'-bi-1H-tetrazoledisodium salt is such that the molar ratio (G/A) of the ammonia (G) to the hydrogen cyanide or the sodium cyanide (A) used for the synthesis is from 0.01 to 0.16.

17. The process according to claim 2 wherein the acidic substances are organocarboxylic acid comprising acetic acid and formic acid, or mineral acids such as hydrochloric acid, sulfuric acid and nitric acid.

18. The process according to claim 16 wherein the acidic substances are organocarboxylic acids such as acetic acid and formic acid, or mineral acids comprising hydrochloric acid, sulfuric acid and nitric acid.

19. The process according to claim 5 wherein treatment with the chelating resin and filtration of the copper.ammonia.5,5'-bi-1H-tetrazole complex is conducted at a temperature of not lower that 40° C.

20. The process according to claim 18 wherein treatment with the chelating resin and filtration of the copper.ammonia.5,5'-bi-1H-tetrazole complex is conducted at a temperature of not lower that 40° C.

21. The process according to claim 7 wherein treatment with the chelating resin and filtration of the copper.ammonia.5,5'-bi-1H-tetrazole complex is conducted at a temperature of not lower that 40° C.

\* \* \* \* \*